US009399118B2

(12) United States Patent
Kume et al.

(10) Patent No.: US 9,399,118 B2
(45) Date of Patent: Jul. 26, 2016

(54) METHODS AND DEVICES FOR TRANSCAROTID ACCESS

(71) Applicant: Silk Road Medical, Inc., Sunnyvale, CA (US)

(72) Inventors: Stewart M. Kume, Sunnyvale, CA (US); Michi E. Garrison, Sunnyvale, CA (US); Michael P. Wallace, Sunnyvale, CA (US); Herbert Mendoza, Sunnyvale, CA (US); Marlon Moreno, Sunnyvale, CA (US)

(73) Assignee: Silk Road Medical, Inc., Sunnyvale, CA (US)

( * ) Notice: Subject to any disclaimer, the term of this patent is extended or adjusted under 35 U.S.C. 154(b) by 0 days.

(21) Appl. No.: 15/005,770

(22) Filed: Jan. 25, 2016

(65) Prior Publication Data
US 2016/0158502 A1    Jun. 9, 2016

Related U.S. Application Data

(63) Continuation of application No. 14/575,199, filed on Dec. 18, 2014, now Pat. No. 9,126,018, which is a continuation of application No. 14/537,316, filed on Nov. 10, 2014, now Pat. No. 9,241,699.

(60) Provisional application No. 62/075,169, filed on Nov. 4, 2014, provisional application No. 62/046,112, filed on Sep. 4, 2014.

(51) Int. Cl.
*A61M 25/06* (2006.01)
*A61M 25/01* (2006.01)
(Continued)

(52) U.S. Cl.
CPC ....... *A61M 25/0606* (2013.01); *A61M 25/0108* (2013.01); *A61M 25/09* (2013.01); *A61M 29/02* (2013.01); *A61M 2025/0681* (2013.01); *A61M 2025/0687* (2013.01)

(58) Field of Classification Search
CPC .................................................. A61M 25/0606
See application file for complete search history.

(56) References Cited

U.S. PATENT DOCUMENTS 4,771,777 A   9/1988  Horzewski et al.
4,840,690 A   6/1989  Melinyshyn et al.
(Continued)

FOREIGN PATENT DOCUMENTS

DE   102006039236 A1   2/2008
EP       0427429 A2   5/1991
(Continued)

OTHER PUBLICATIONS

Adami, M.D., et al., (2002) "Use of the Parodi Anti-Embolism System in Carotid Stenting: Italian Trial Results" J Endovasc Ther 9:147-154.
(Continued)

*Primary Examiner* — Andrew Yang
(74) *Attorney, Agent, or Firm* — Fred C. Hernandez; Mintz Levin Cohn Ferris Glovsky and Popeo, P.C.

(57) ABSTRACT

Disclosed is an arterial access sheath for introducing an interventional device into an artery. The arterial access sheath includes an elongated body sized and shaped to be transcervically introduced into a common carotid artery at an access location in the neck and an internal lumen in the elongated body having a proximal opening in a proximal region of the elongated body and a distal opening in a distal region of the elongated body. The internal lumen provides a passageway for introducing an interventional device into the common carotid artery when the elongated body is positioned in the common carotid artery. The elongated body has a proximal section and a distalmost section that is more flexible than the proximal section. A ratio of an entire length of the distalmost section to an overall length of the sheath body is one tenth to one half the overall length of the sheath body.

22 Claims, 11 Drawing Sheets

(51) Int. Cl.
*A61M 29/02* (2006.01)
*A61M 25/09* (2006.01)

(56) References Cited

U.S. PATENT DOCUMENTS

| | | |
|---|---|---|
| 4,865,581 A | 9/1989 | Lundquist et al. |
| 4,921,478 A | 5/1990 | Solano et al. |
| 4,921,479 A | 5/1990 | Grayzel |
| 4,946,440 A | 8/1990 | Hall |
| 5,135,484 A | 8/1992 | Wright |
| 5,250,060 A | 10/1993 | Carbo et al. |
| 5,312,356 A | 5/1994 | Engelson et al. |
| RE34,633 E | 6/1994 | Sos et al. |
| 5,324,262 A | 6/1994 | Fischell et al. |
| 5,328,471 A | 7/1994 | Slepian |
| 5,380,284 A | 1/1995 | Don Michael |
| 5,429,605 A | 7/1995 | Bernd et al. |
| 5,437,632 A | 8/1995 | Engelson |
| 5,443,454 A | 8/1995 | Tanabe et al. |
| 5,454,795 A | 10/1995 | Samson |
| 5,476,450 A | 12/1995 | Ruggio |
| 5,484,412 A | 1/1996 | Pierpont |
| 5,484,418 A | 1/1996 | Quiachon et al. |
| 5,492,530 A | 2/1996 | Fischell et al. |
| 5,496,294 A | 3/1996 | Hergenrother et al. |
| 5,522,836 A | 6/1996 | Palermo |
| 5,542,937 A | 8/1996 | Chee et al. |
| 5,558,635 A | 9/1996 | Cannon |
| 5,573,520 A | 11/1996 | Schwartz et al. |
| 5,599,326 A | 2/1997 | Carter |
| 5,628,754 A | 5/1997 | Shevlin et al. |
| 5,658,264 A | 8/1997 | Samson |
| 5,667,499 A | 9/1997 | Welch et al. |
| 5,695,483 A | 12/1997 | Samson |
| 5,702,373 A | 12/1997 | Samson |
| 5,707,376 A | 1/1998 | Kavteladze et al. |
| 5,730,734 A | 3/1998 | Adams et al. |
| 5,749,849 A | 5/1998 | Engelson |
| 5,749,858 A | 5/1998 | Cramer |
| 5,794,629 A | 8/1998 | Frazee |
| 5,795,341 A | 8/1998 | Samson |
| 5,810,869 A | 9/1998 | Kaplan et al. |
| 5,827,229 A | 10/1998 | Auth et al. |
| 5,833,650 A | 11/1998 | Imran |
| 5,836,926 A | 11/1998 | Peterson et al. |
| 5,846,251 A | 12/1998 | Hart |
| 5,851,210 A | 12/1998 | Torossian |
| 5,853,400 A | 12/1998 | Samson |
| 5,876,367 A | 3/1999 | Kaganov et al. |
| 5,876,386 A | 3/1999 | Samson |
| 5,882,334 A | 3/1999 | Sepetka et al. |
| 5,895,399 A | 4/1999 | Barbut et al. |
| 5,908,407 A | 6/1999 | Frazee et al. |
| 5,913,848 A | 6/1999 | Luther et al. |
| 5,916,208 A | 6/1999 | Luther et al. |
| 5,921,952 A | 7/1999 | Desmond, III et al. |
| 5,928,192 A | 7/1999 | Maahs |
| 5,935,122 A | 8/1999 | Fourkas et al. |
| 5,938,645 A | 8/1999 | Gordon |
| 5,957,882 A | 9/1999 | Nita et al. |
| 5,976,093 A | 11/1999 | Jang |
| 5,976,178 A | 11/1999 | Goldsteen et al. |
| 5,997,508 A | 12/1999 | Lunn et al. |
| 6,004,310 A | 12/1999 | Bardsley et al. |
| 6,013,085 A | 1/2000 | Howard |
| 6,022,340 A | 2/2000 | Sepetka et al. |
| 6,030,369 A | 2/2000 | Engelson et al. |
| 6,033,388 A | 3/2000 | Nordstrom et al. |
| 6,044,845 A | 4/2000 | Lewis |
| 6,053,903 A | 4/2000 | Samson |
| 6,053,904 A | 4/2000 | Scribner et al. |
| 6,071,263 A | 6/2000 | Kirkman |
| 6,074,357 A | 6/2000 | Kaganov et al. |
| 6,074,398 A | 6/2000 | Leschinsky |
| 6,090,072 A | 7/2000 | Kratoska et al. |
| 6,110,139 A | 8/2000 | Loubser |
| 6,139,524 A | 10/2000 | Killion |
| 6,146,370 A | 11/2000 | Barbut |
| 6,146,373 A | 11/2000 | Cragg et al. |
| 6,146,415 A | 11/2000 | Fitz |
| 6,152,909 A | 11/2000 | Bagaoisan et al. |
| 6,152,912 A | 11/2000 | Jansen et al. |
| 6,159,230 A | 12/2000 | Samuels |
| 6,161,547 A | 12/2000 | Barbut |
| 6,165,199 A | 12/2000 | Barbut |
| 6,176,844 B1 | 1/2001 | Lee |
| 6,197,016 B1 | 3/2001 | Fourkas et al. |
| 6,206,868 B1 | 3/2001 | Parodi |
| 6,210,370 B1 | 4/2001 | Chi-Sing et al. |
| 6,234,971 B1 | 5/2001 | Jang |
| 6,254,628 B1 | 7/2001 | Wallace et al. |
| 6,258,080 B1 | 7/2001 | Samson |
| 6,270,477 B1 | 8/2001 | Bagaoisan et al. |
| 6,277,139 B1 | 8/2001 | Levinson et al. |
| 6,287,319 B1 | 9/2001 | Aboul-Hosn et al. |
| 6,295,989 B1 | 10/2001 | Connors, III |
| 6,295,990 B1 | 10/2001 | Lewis et al. |
| 6,306,106 B1 | 10/2001 | Boyle |
| 6,306,163 B1 | 10/2001 | Fitz |
| 6,364,900 B1 | 4/2002 | Heuser |
| 6,368,316 B1 | 4/2002 | Jansen et al. |
| 6,368,344 B1 | 4/2002 | Fitz |
| 6,379,325 B1 | 4/2002 | Benett et al. |
| 6,383,172 B1 | 5/2002 | Barbut |
| 6,413,235 B1 | 7/2002 | Parodi |
| 6,423,032 B2 | 7/2002 | Parodi |
| 6,423,086 B1 | 7/2002 | Barbut et al. |
| 6,428,531 B1 | 8/2002 | Visuri et al. |
| 6,435,189 B1 | 8/2002 | Lewis et al. |
| 6,436,087 B1 | 8/2002 | Lewis et al. |
| 6,454,741 B1 | 9/2002 | Muni et al. |
| 6,458,151 B1 | 10/2002 | Saltiel |
| 6,464,664 B1 | 10/2002 | Jonkman et al. |
| 6,481,439 B1 | 11/2002 | Lewis et al. |
| 6,482,172 B1 | 11/2002 | Thramann |
| 6,482,217 B1 | 11/2002 | Pintor et al. |
| 6,508,824 B1 | 1/2003 | Flaherty et al. |
| 6,517,520 B2 | 2/2003 | Chang et al. |
| 6,527,746 B1 | 3/2003 | Oslund et al. |
| 6,533,800 B1 | 3/2003 | Barbut |
| 6,540,712 B1 | 4/2003 | Parodi et al. |
| 6,544,276 B1 | 4/2003 | Azizi |
| 6,551,268 B1 | 4/2003 | Kaganov et al. |
| 6,555,057 B1 | 4/2003 | Barbut et al. |
| 6,562,049 B1 | 5/2003 | Norlander et al. |
| 6,562,052 B2 | 5/2003 | Nobles et al. |
| 6,582,390 B1 | 6/2003 | Sanderson |
| 6,582,396 B1 | 6/2003 | Parodi |
| 6,582,448 B1 | 6/2003 | Boyle et al. |
| 6,595,953 B1 | 7/2003 | Coppi et al. |
| 6,595,980 B1 | 7/2003 | Barbut |
| 6,605,074 B2 | 8/2003 | Zadno-Azizi et al. |
| 6,612,999 B2 | 9/2003 | Brennan et al. |
| 6,623,471 B1 | 9/2003 | Barbut |
| 6,623,491 B2 | 9/2003 | Thompson |
| 6,623,518 B2 | 9/2003 | Thompson et al. |
| 6,626,886 B1 | 9/2003 | Barbut |
| 6,632,236 B2 | 10/2003 | Hogendijk |
| 6,635,070 B2 | 10/2003 | Leeflang et al. |
| 6,638,243 B2 | 10/2003 | Kupiecki |
| 6,638,245 B2 | 10/2003 | Miller et al. |
| 6,641,573 B1 | 11/2003 | Parodi |
| 6,645,160 B1 | 11/2003 | Heesch |
| 6,645,222 B1 | 11/2003 | Parodi et al. |
| 6,652,480 B1 | 11/2003 | Imran et al. |
| 6,656,152 B2 | 12/2003 | Putz |
| 6,663,650 B2 | 12/2003 | Sepetka et al. |
| 6,663,652 B2 | 12/2003 | Daniel et al. |
| 6,679,893 B1 | 1/2004 | Tran |
| 6,682,505 B2 | 1/2004 | Bates et al. |
| 6,685,722 B1 | 2/2004 | Rosenbluth et al. |
| 6,702,782 B2 | 3/2004 | Miller et al. |
| 6,711,436 B1 | 3/2004 | Duhaylongsod |
| 6,719,717 B1 | 4/2004 | Johnson et al. |

(56) References Cited

U.S. PATENT DOCUMENTS

| | | |
|---|---|---|
| 6,730,104 B1 | 5/2004 | Sepetka et al. |
| 6,733,517 B1 | 5/2004 | Collins |
| 6,749,627 B2 | 6/2004 | Thompson et al. |
| 6,755,847 B2 | 6/2004 | Eskuri |
| 6,758,854 B1 | 7/2004 | Butler et al. |
| 6,764,464 B2 | 7/2004 | McGuckin, Jr. et al. |
| 6,790,204 B2 | 9/2004 | Zadno-Azizi et al. |
| 6,824,545 B2 | 11/2004 | Sepetka et al. |
| 6,827,730 B1 | 12/2004 | Leschinsky |
| 6,837,881 B1 | 1/2005 | Barbut |
| 6,840,949 B2 | 1/2005 | Barbut |
| 6,849,068 B1 | 2/2005 | Bagaoisan et al. |
| 6,855,136 B2 | 2/2005 | Dorros et al. |
| 6,884,235 B2 | 4/2005 | McGuckin, Jr. et al. |
| 6,902,540 B2 | 6/2005 | Dorros et al. |
| 6,905,490 B2 | 6/2005 | Parodi |
| 6,905,505 B2 | 6/2005 | Nash et al. |
| 6,908,474 B2 | 6/2005 | Hogendijk et al. |
| 6,929,632 B2 | 8/2005 | Nita et al. |
| 6,929,634 B2 | 8/2005 | Dorros et al. |
| 6,936,060 B2 | 8/2005 | Hogendijk et al. |
| 6,958,059 B2 | 10/2005 | Zadno-Azizi |
| 6,960,189 B2 | 11/2005 | Bates et al. |
| 6,972,030 B2 | 12/2005 | Lee et al. |
| 7,001,400 B1 | 2/2006 | Modesitt et al. |
| 7,004,924 B1 | 2/2006 | Brugger et al. |
| 7,004,931 B2 | 2/2006 | Hogendijk |
| 7,004,952 B2 | 2/2006 | Nobles et al. |
| 7,022,100 B1 | 4/2006 | Aboul-Hosn et al. |
| 7,029,488 B2 | 4/2006 | Schonholz et al. |
| 7,033,336 B2 | 4/2006 | Hogendijk |
| 7,033,344 B2 | 4/2006 | Imran |
| 7,048,758 B2 | 5/2006 | Boyle et al. |
| 7,063,714 B2 | 6/2006 | Dorros et al. |
| 7,083,594 B2 | 8/2006 | Coppi |
| 7,104,979 B2 | 9/2006 | Jansen et al. |
| 7,108,677 B2 | 9/2006 | Courtney et al. |
| 7,144,386 B2 | 12/2006 | Korkor et al. |
| 7,150,712 B2 | 12/2006 | Buehlmann et al. |
| 7,152,605 B2 | 12/2006 | Khairkhahan et al. |
| 7,166,088 B2 | 1/2007 | Heuser |
| 7,169,165 B2 | 1/2007 | Belef et al. |
| 7,172,621 B2 | 2/2007 | Theron |
| 7,223,253 B2 | 5/2007 | Hogendijk |
| 7,232,452 B2 | 6/2007 | Adams et al. |
| 7,250,042 B2 | 7/2007 | Kataishi et al. |
| 7,306,585 B2 | 12/2007 | Ross |
| 7,309,334 B2 | 12/2007 | von Hoffmann |
| 7,367,982 B2 | 5/2008 | Nash et al. |
| 7,374,560 B2 | 5/2008 | Ressemann et al. |
| 7,374,561 B2 | 5/2008 | Barbut |
| 7,384,412 B2 | 6/2008 | Coppi |
| 7,402,151 B2 | 7/2008 | Rosenman et al. |
| 7,422,579 B2 | 9/2008 | Wahr et al. |
| 7,458,980 B2 | 12/2008 | Barbut |
| 7,497,844 B2 * | 3/2009 | Spear .................. A61B 18/1492 604/164.01 |
| 7,524,303 B1 | 4/2009 | Don Michael et al. |
| 7,534,250 B2 | 5/2009 | Schaeffer et al. |
| 7,731,683 B2 | 6/2010 | Jang et al. |
| 7,766,049 B2 | 8/2010 | Miller et al. |
| 7,766,820 B2 | 8/2010 | Core |
| 7,806,906 B2 | 10/2010 | Don Michael |
| 7,815,626 B1 | 10/2010 | McFadden et al. |
| 7,842,065 B2 | 11/2010 | Belef et al. |
| 7,867,216 B2 | 1/2011 | Wahr et al. |
| 7,905,856 B2 | 3/2011 | McGuckin, Jr. et al. |
| 7,905,877 B1 | 3/2011 | Jimenez et al. |
| 7,909,812 B2 | 3/2011 | Jansen et al. |
| 7,927,309 B2 | 4/2011 | Palm |
| 7,927,347 B2 | 4/2011 | Hogendijk et al. |
| 7,972,308 B2 | 7/2011 | Putz |
| 7,998,104 B2 | 8/2011 | Chang |
| 8,029,533 B2 | 10/2011 | Bagaoisan et al. |
| 8,052,640 B2 | 11/2011 | Fiorella et al. |
| 8,066,757 B2 | 11/2011 | Ferrera et al. |
| 8,142,413 B2 | 3/2012 | Root et al. |
| RE43,300 E | 4/2012 | Saadat et al. |
| 8,152,782 B2 | 4/2012 | Jang et al. |
| 8,157,760 B2 | 4/2012 | Criado et al. |
| 8,181,324 B2 | 5/2012 | McFadden et al. |
| 8,221,348 B2 | 7/2012 | Hackett et al. |
| 8,231,600 B2 | 7/2012 | von Hoffmann |
| 8,252,010 B1 | 8/2012 | Raju et al. |
| 8,292,850 B2 | 10/2012 | Root et al. |
| 8,343,089 B2 | 1/2013 | Chang |
| 8,414,516 B2 | 4/2013 | Chang |
| 8,545,552 B2 | 10/2013 | Garrison et al. |
| 8,574,245 B2 | 11/2013 | Garrison et al. |
| 8,870,805 B2 | 10/2014 | Chang |
| 8,961,549 B2 | 2/2015 | Conn |
| 2001/0044598 A1 | 11/2001 | Parodi |
| 2001/0049486 A1 | 12/2001 | Evans et al. |
| 2001/0049517 A1 | 12/2001 | Zadno-Azizi et al. |
| 2002/0087119 A1 | 7/2002 | Parodi |
| 2002/0128679 A1 | 9/2002 | Turovskiy et al. |
| 2002/0133111 A1 | 9/2002 | Shadduck |
| 2002/0151922 A1 | 10/2002 | Hogendijk et al. |
| 2002/0156455 A1 | 10/2002 | Barbut |
| 2002/0156460 A1 | 10/2002 | Ye et al. |
| 2002/0165598 A1 | 11/2002 | Wahr et al. |
| 2002/0173815 A1 | 11/2002 | Hogendijk et al. |
| 2002/0183783 A1 | 12/2002 | Shadduck |
| 2003/0040762 A1 | 2/2003 | Dorros et al. |
| 2003/0065356 A1 | 4/2003 | Tsugita et al. |
| 2003/0069468 A1 | 4/2003 | Bolling et al. |
| 2003/0078562 A1 | 4/2003 | Makower et al. |
| 2003/0186203 A1 | 10/2003 | Aboud |
| 2003/0212304 A1 | 11/2003 | Lattouf |
| 2003/0212384 A1 | 11/2003 | Hayden |
| 2004/0059243 A1 | 3/2004 | Flores et al. |
| 2004/0116878 A1 | 6/2004 | Byrd et al. |
| 2004/0133232 A1 | 7/2004 | Rosenbluth et al. |
| 2004/0138608 A1 | 7/2004 | Barbut et al. |
| 2004/0210194 A1 | 10/2004 | Bonnette et al. |
| 2005/0131453 A1 | 6/2005 | Parodi |
| 2005/0154344 A1 | 7/2005 | Chang |
| 2005/0154349 A1 | 7/2005 | Renz et al. |
| 2005/0209559 A1 | 9/2005 | Thornton et al. |
| 2005/0273051 A1 | 12/2005 | Coppi |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0089618 A1 | 4/2006 | McFerran et al. |
| 2006/0135961 A1 | 6/2006 | Rosenman et al. |
| 2006/0200191 A1 | 9/2006 | Zadno-Azizi |
| 2006/0271098 A1 | 11/2006 | Peacock |
| 2007/0021778 A1 | 1/2007 | Carly |
| 2007/0173784 A1 | 7/2007 | Johansson et al. |
| 2007/0197956 A1 | 8/2007 | Le et al. |
| 2007/0198028 A1 | 8/2007 | Miloslavski et al. |
| 2007/0198049 A1 | 8/2007 | Barbut |
| 2008/0082107 A1 | 4/2008 | Miller et al. |
| 2008/0140010 A1 | 6/2008 | Kennedy et al. |
| 2008/0177245 A1 | 7/2008 | Mesallum |
| 2008/0200946 A1 | 8/2008 | Braun et al. |
| 2009/0018455 A1 | 1/2009 | Chang |
| 2009/0024072 A1 | 1/2009 | Criado et al. |
| 2009/0030400 A1 | 1/2009 | Bose et al. |
| 2009/0198172 A1 | 8/2009 | Garrison et al. |
| 2009/0254166 A1 | 10/2009 | Chou et al. |
| 2009/0299393 A1 | 12/2009 | Martin et al. |
| 2010/0004607 A1 | 1/2010 | Wilson et al. |
| 2010/0042118 A1 | 2/2010 | Garrison et al. |
| 2010/0063479 A1 | 3/2010 | Merdan et al. |
| 2010/0063480 A1 | 3/2010 | Shireman |
| 2010/0094330 A1 | 4/2010 | Barbut |
| 2010/0114017 A1 | 5/2010 | Lenker et al. |
| 2010/0145308 A1 | 6/2010 | Layman et al. |
| 2010/0185216 A1 | 7/2010 | Garrison et al. |
| 2010/0204672 A1 | 8/2010 | Lockhart et al. |
| 2010/0204684 A1 | 8/2010 | Garrison et al. |
| 2010/0217276 A1 | 8/2010 | Garrison et al. |
| 2010/0228269 A1 | 9/2010 | Garrison et al. |

(56) References Cited

U.S. PATENT DOCUMENTS

| | | |
|---|---|---|
| 2010/0256600 A1 | 10/2010 | Ferrera |
| 2010/0318097 A1 | 12/2010 | Ferrera et al. |
| 2011/0009875 A1 | 1/2011 | Grandfield et al. |
| 2011/0034986 A1 | 2/2011 | Chou et al. |
| 2011/0087147 A1 | 4/2011 | Garrison et al. |
| 2011/0112567 A1 | 5/2011 | Lenker et al. |
| 2011/0125181 A1 | 5/2011 | Brady et al. |
| 2011/0152760 A1 | 6/2011 | Parker |
| 2011/0238041 A1 | 9/2011 | Lim et al. |
| 2012/0310212 A1 | 12/2012 | Fischell et al. |
| 2013/0035628 A1 | 2/2013 | Garrison et al. |
| 2013/0184735 A1 | 7/2013 | Fischell et al. |
| 2013/0281788 A1* | 10/2013 | Garrison ............ A61B 17/3415 600/208 |
| 2014/0257186 A1 | 9/2014 | Kerr |
| 2014/0296769 A1* | 10/2014 | Hyde .................. A61M 27/002 604/9 |
| 2014/0296868 A1 | 10/2014 | Garrison et al. |
| 2015/0173782 A1* | 6/2015 | Garrison ........... A61M 25/0054 606/127 |
| 2015/0174368 A1 | 6/2015 | Garrison et al. |

FOREIGN PATENT DOCUMENTS

| | | |
|---|---|---|
| EP | 1440663 A1 | 7/2004 |
| WO | WO-95/05209 A1 | 2/1995 |
| WO | WO-98/38930 A1 | 9/1998 |
| WO | WO-99/45835 A2 | 9/1999 |
| WO | WO-00/32266 A1 | 6/2000 |
| WO | WO-00/76390 A2 | 12/2000 |
| WO | WO-01/58365 A1 | 8/2001 |
| WO | WO-02/32495 A1 | 4/2002 |
| WO | WO-03/090831 A2 | 11/2003 |
| WO | WO-2004/006803 A1 | 1/2004 |
| WO | WO-2005/051206 A1 | 6/2005 |
| WO | WO-2008/144587 A2 | 11/2008 |
| WO | WO-2009/012473 A3 | 1/2009 |
| WO | WO-2009/099764 A1 | 8/2009 |
| WO | WO-2009/100210 A1 | 8/2009 |
| WO | WO-2010/075445 A1 | 7/2010 |
| WO | WO-2012/047803 A2 | 4/2012 |

OTHER PUBLICATIONS

Bergeron et al. (1999). "Percutaneous stenting of the internal carotid artery: the European CAST I Study" J. Endovasc. Surg. 6:155-159.
Bergeron et al. (2008) MEET Presentation, Cannes, French Riviera "Why I do not use routine femoral access for CAS".
Bergeron P. et al. (1996) "Recurrent Carotid Disease: Will Stents be an alternative to surgery?" J Endovasc Surg; 3: 76-79.
Bourekas, E. C., A. P. Slivka, et al. (2004). "Intraarterial thrombolytic therapy within 3 hours of the onset of stroke." Neurosurgery 54(1): 39-44; discussion 44-6.
Cohen et al., "A reappraisal of the common carotid artery as an access site in interventional procedures for acute stroke therapies", Case Reports, Journal of Clinical Neuroscience 19 (2012) pp. 323-326.
Criado et al. (1997) "Evolving indications for and early results of carotid artery stenting" Am. J. Surg.; 174:111-114.
Diederich et al. (2004) "First Clinical experiences with an endovascular clamping system for neuroprotection during carotid stenting" Eur. J. Vasc. Endovasc. Surg. 28:629-633.
Diethrich et al., (1996). "Percutaneous techniques for endoluminal carotid interventions" J. Endovasc. Surg. 3:182-202.
Diethrich, E. B. (2004). The Direct Cervical Carotid Artery Approach. Carotid Artery Stenting: Current Practice and Techniques. N. Al-Mubarak, G. S. Roubin, S. Iyer and J. Vitek. Philadephia, Lippincott Williams & Wilkins: Chapter 11. pp. 124-136.
Feldtman, R. W., C. J. Buckley, et al. (2006). "How I do it: cervical access for carotid artery stenting." Am J Surg 192(6): 779-81.
Fiorella, D., M. Kelly, et al. (2008). "Endovascular Treatment of Cerebral Aneurysms." Endovascular Today Jun.

Frazee, J. G. and X. Luo (1999). "Retrograde transvenous perfusion." Crit Care Clin 15(4): 777-88, vii.
Frazee, J. G., X. Luo, et al. (1998). "Retrograde transvenous neuroperfusion: a back door treatment for stroke." Stroke 29(9): 1912-6.
Goldstein "Acute Ischemic Stroke Treatment in 2007" Circ 116:1504-1514 (2007).
Gray et al. (2007) "The CAPTURE registry: Results of carotid stenting with embolic protection in the post approval setting" Cath. Cardiovasc. Interven. 69:341-348.
Henry et al. (1999) "Carotid stenting with cerebral protection: First clinical experience using the PercuSurge GuardWire System" J. Endovasc. Surg. 6:321-331.
Hoffer et al. "Percutaneous Arterial Closure Devices." J. Vasc. Interv. Radiol. 14:865-885 (2003).
Howell, M., K. Doughtery, et al. (2002). "Percutaneous repair of abdominal aortic aneurysms using the AneuRx stent graft and the percutaneous vascular surgery device." Catheter Cardiovasc Interv 55(3): 281-7.
Koebbe, C. J., E. Veznedaroglu, et al. (2006). "Endovascular management of intracranial aneurysms: current experience and future advances." Neurosurgery 59(5 Suppl 3): S93-102; discussion S3-13.
Luebke, T et al. (2007) "Meta-analysis of randomized trials comparing carotid endarterectomy and endovascular treatment" Eur. J. Vasc. Endovasc. Surg. 34:470-479.
MacDonald, S. (2006) "Is there any evidence that cerebral protection is beneficial?" J. Cardiovasc. Surg. 47:127-36.
Mas et al. (2006) "Endarterectomy versus stenting in patients with symptomatic severe carotid stenosis" NEJM 355:1660-71.
MomaPresn (AET) 2002 Biamino, G; MO.MA as a distal protective device, University of Leipzig—Heart Center Department of Clinical and Interventional; Angiology Leipzig, Germany; 2002.
Nesbit, G. M., G. Luh, et al. (2004). "New and future endovascular treatment strategies for acute ischemic stroke." J Vasc Intery Radiol 15(1 Pt 2): S103-10.
Nii, K., K. Kazekawa, et al. (2006). "Direct carotid puncture for the endovascular treatment of anterior circulation aneurysms." AJNR Am J Neuroradiol 27(7): 1502-4.
Ouriel, K., R. K. Greenberg, et al. (2001). "Hemodynamic conditions at the carotid bifurcation during protective common carotid occlusion". J Vasc Surg 34(4): 577-80.
Parodi et al. (2000). "Initial evaluation of carotid angioplasty and stenting with three different cerebral protection devices" J. Vasc. Surg. 32:1127-1136.
Parodi, J. C., L. M. Ferreira, et al. (2005). "Cerebral protection during carotid stenting using flow reversal." J Vasc Surg 41(3): 416-22.
Perez-Arjona, E. A., Z. DelProsto, et al. (2004). "Direct percutaneous carotid artery stenting with distal protection: technical case report." Neurol Res 26(3): 338-41.
Reekers, J. A. (1998). "A balloon protection sheath to prevent peripheral embolization during aortoiliac endovascular procedures." Cardiovasc Intervent Radiol 21(5): 431-3.
Reimers et al. (2005). "Proximal endovascular flow blockage for cerebral protection during carotid artery stenting: Results froma prospective multicenter registry" J. Endovasc. Ther. 12:156-165.
Ribo, M., C. Molina, et al. (2008). "Buying Time for Recanalization in Acute Stroke: Arterial Blood Infusion Beyond the Occluding Clot as a Neuroprotective Strategy". J Neuroimaging.
Ross, I. B. and G. D. Luzardo (2006). "Direct access to the carotid circulation by cut down for endovascular neuro-interventions." Surg Neurol 65(2): 207-11; discussion 211.
Stejskal, et al., "Experience of 500 Cases of Neurophysiological Monitoring in Carotid Endarterectomy", Acta Neurochir, 2007, 149:681-689.
Theron, et al. "New Triple Coaxial Catheter System for Carotid Angioplasty with Cerebral Protection.". AJNR 11:869-874, Sep./Oct. 1990. 0195-6108/90/1106-0869. American Society of Neurology.

* cited by examiner

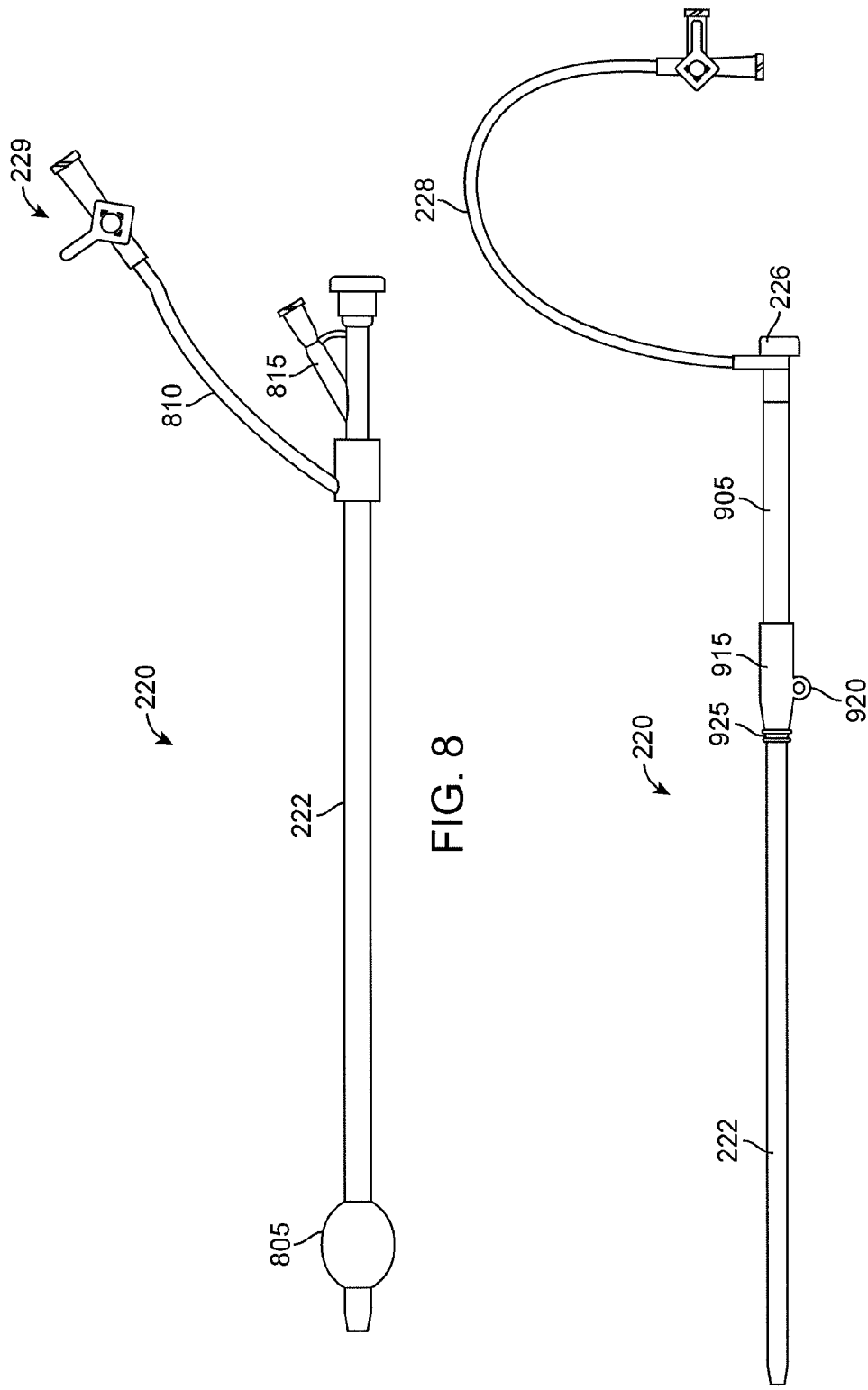

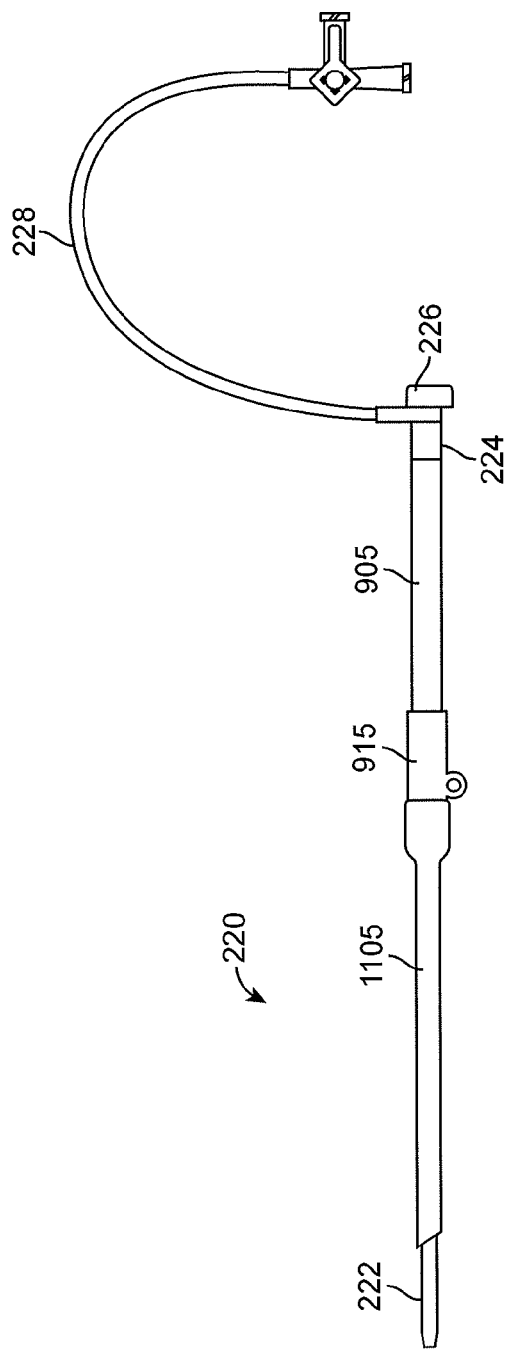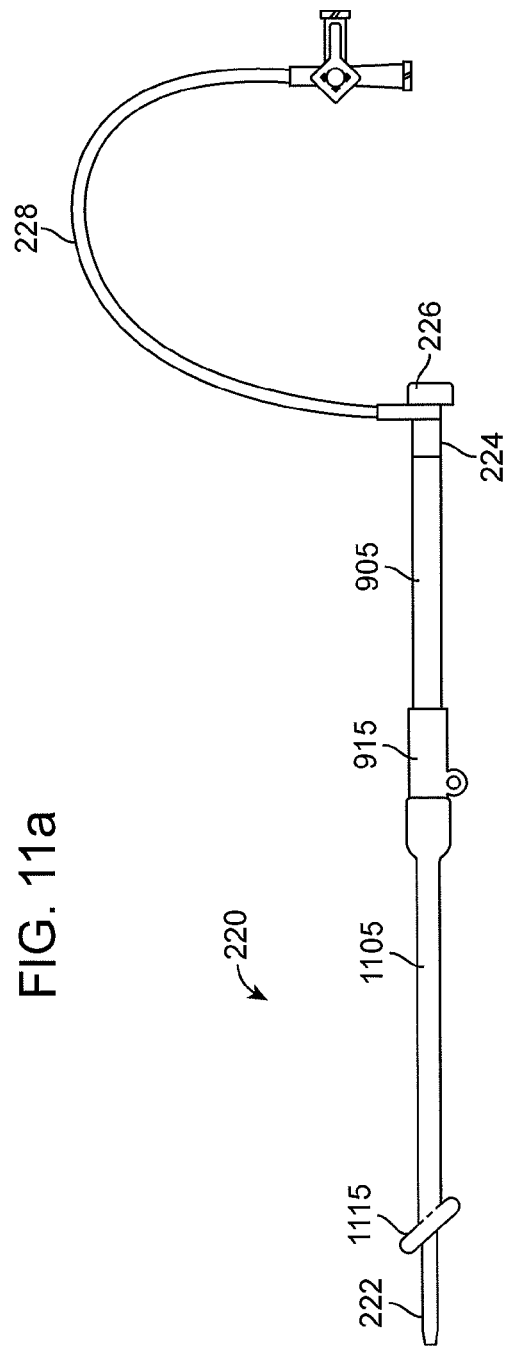
FIG. 11a
FIG. 11b

METHODS AND DEVICES FOR TRANSCAROTID ACCESS

REFERENCE TO PRIORITY DOCUMENT

This application is continuation of U.S. patent application Ser. No. 14/575,199 entitled "Methods and Devices for Transcarotid Access" filed Dec. 18, 2014, which is a continuation of U.S. patent application Ser. No. 14/537,316 entitled "Methods And Devices For Transcarotid Access" filed Nov. 10, 2014, which claims the benefit of priority to U.S. Provisional Application Ser. No. 62/046,112, entitled "METHODS AND DEVICES FOR TRANSCAROTID ACCESS" filed on Sep. 4, 2014, and U.S. Provisional Application Ser. No. 62/075,169, entitled "METHODS AND DEVICES FOR TRANSCAROTID ACCESS" filed on Nov. 4, 2014. Priority of the aforementioned filing dates is claimed and the patent applications are incorporated herein by reference in their entirety.

BACKGROUND

The present disclosure relates generally to medical methods, systems, and devices for performing endovascular interventions. More particularly, the present disclosure relates to methods and systems for access directly into the carotid artery to perform interventional procedures in the treatment of vascular disease and other diseases associated with the vasculature.

Interventional procedures are performed to treat vascular disease, for example stenosis, occlusions, aneurysms, or fistulae. Interventional procedures are also used to perform procedures on organs or tissue targets that are accessible via blood vessels, for example denervation or ablation of tissue to intervene in nerve conduction, embolization of vessels to restrict blood flow to tumors or other tissue, and delivery of drugs, contrast, or other agents to intra or extravascular targets for therapeutic or diagnostic purposes. Interventional procedures are typically divided into coronary, neurovascular, and peripheral vascular categories. Most procedures are performed in the arterial system via an arterial access site.

Methods for gaining arterial access to perform these procedures are well-established, and fall into two broad categories: percutaneous access and surgical cut-down. The majority of interventional procedures utilize a percutaneous access. For this access method, a needle puncture is made from the skin, through the subcutaneous tissue and muscle layers to the vessel wall, and into the vessel itself. Vascular ultrasound is often used to image the vessel and surrounding structures, and facilitate accurate insertion of the needle into the vessel. Depending on the size of the artery and of the access device, the method will vary, for example a Seldinger technique or modified Seldinger technique consists of placing a sheath guide wire through the needle into the vessel. Typically the sheath guide wire is 0.035" or 0.038". In some instances, a micro-puncture or micro access technique is used whereby the vessel is initially accessed by a small gauge needle, and successively dilated up by a 4F micropuncture cannula through which the sheath guidewire is placed. Once the guidewire is placed, an access sheath and sheath dilator are inserted over the guide wire into the artery. In other instances, for example if a radial artery is being used as an access site, a smaller sheath guidewire is used through the initial needle puncture, for example an 0.018" guidewire. The dilator of a radial access sheath is designed to accommodate this smaller size guidewire, so that the access sheath and dilator can be inserted over the 0.018" wire into the artery.

In a surgical cut-down, a skin incision is made and tissue is dissected away to the level of the target artery. This method is often used if the procedure requires a large access device, if there is risk to the vessel with a percutaneous access, and/or if there is possibility of unreliable closure at the access site at the conclusion of the procedure. Depending on the size of the artery and of the access device, an incision is made into the wall of the vessel with a blade, or the vessel wall is punctured directly by an access needle, through which a sheath guide wire is placed. The micropuncture technique may also be used to place a sheath guide wire. As above, the access sheath and sheath dilator are inserted into the artery over the sheath guide wire. Once the access sheath is placed, the dilator and sheath guide wire are removed. Devices can now be introduced via the access sheath into the artery and advanced using standard interventional techniques and fluoroscopy to the target site to perform the procedure.

Access to the target site is accomplished from an arterial access site that is easily entered from the skin. Usually this is the femoral artery which is both relatively large and relatively superficial, and easy to close on completion of the procedure using either direct compression or one of a variety of vessel closure devices. For this reason, endovascular devices are specifically designed for this femoral access site. However, the femoral artery and its vicinity are sometimes diseased, making it difficult or impossible to safely access or introduce a device into the vasculature from this site. In addition, the treatment target site may be quite some distance from the femoral access point requiring devices to be quite lengthy and cumbersome. Further, reaching the target site form the femoral access point may involve traversing tortuous and/or diseased arteries, which adds time and risk to the procedure. For these reasons, alternate access sites are sometimes employed. These include the radial, brachial and axillary arteries. However, these access sites are not always ideal, as they involve smaller arteries and may also include tortuous segments and some distance between the access and target sites.

Some Exemplary Issues with Current Technology

In some instances, a desired access site is the carotid artery. For example, procedures to treat disease at the carotid artery bifurcation and internal carotid artery are quite close to this access site. Procedures in the intracranial and cerebral arteries are likewise much closure to this access site than the femoral artery. This artery is also larger than some of the alternate access arteries noted above. (The common carotid artery is typically 6 to 10 mm in diameter, the radial artery is 2 to 3 mm in diameter.)

Because most access devices used in interventional procedure are designed for the femoral access, these devices are not ideal for the alternate carotid access sites, both in length and mechanical properties. This makes the procedure more cumbersome and in some cases more risky if using devices designed for femoral access in a carotid access procedure. For example, in some procedures it is desirable to keep the distal tip of the access sheath below or away from the carotid bifurcation, for example in procedures involving placing a stent at the carotid bifurcation. For patients with a low bifurcation, a short neck, or a very deep carotid artery, the angle of entry of the sheath into the artery (relative to the longitudinal axis of the artery) is very acute with respect to the longitudinal axis of the artery, i.e. more perpendicular than parallel relative to the longitudinal axis of the artery. This acute angle increases the difficulty and risk in sheath insertion and in insertion of devices through the sheath. In these procedures, there is also risk of the sheath dislodgement as only a minimal length of sheath can be inserted. In femoral or radial access cases, the sheaths are typically inserted into the artery all the way to the hub of the sheath, making sheath position very secure and parallel to the artery, so that the issues with steep insertion angle and sheath dislodgement do not occur in femoral access sites.

In other procedures, it is desirable to position the sheath tip up to and possibly including the petrous portion of the internal carotid artery, for example in procedures requiring access to cerebral vessels. Conventional interventional sheaths and sheath dilators are not flexible enough to be safely positioned at this site.

In addition, radiation exposure may be a problem for the hands of the operators for procedures utilizing a transcarotid access site, if the working areas are close to the access site.

SUMMARY

What is needed is a system of devices that optimize ease and safety of arterial access directly into the common carotid artery. What is also needed is a system of devices which minimize radiation exposure to the operator. What are also needed are methods for safe and easy access into the carotid artery to perform peripheral and neurovascular interventional procedures.

Disclosed are methods and devices that enable safe, rapid and relatively short and straight transcarotid access to the arterial vasculature to treat coronary, peripheral and neurovascular disease states. The devices and associated methods include transcarotid access devices, guide catheters, catheters, and guide wires specifically to reach a target anatomy via a transcarotid access site. Included in this disclosure are kits of various combinations of these devices to facilitate multiple types of transcarotid interventional procedures.

In one aspect, there is disclosed a system of devices for accessing a carotid artery via a direct puncture of the carotid arterial wall, comprising a sheath guide wire, an arterial access sheath and a sheath dilator, wherein the arterial access sheath and sheath dilator are sized and configured to be inserted in combination over the sheath guide wire directly into the common carotid artery, and wherein the sheath has an internal lumen and a proximal port such that the lumen provides a passageway for an interventional device to be inserted via the proximal port into the carotid artery.

In another aspect, the system for accessing a carotid artery also includes: an access needle, an access guide wire, and an access cannula, all sized and configured to insert a sheath guide wire into the wall of the carotid artery so that the arterial access sheath and dilator may be placed either percutaneously or via a surgical cut down.

In another aspect, there is disclosed a method for treatment of coronary, peripheral or neurovascular disease, comprising: forming a penetration in a wall of a carotid artery; positioning an arterial access sheath through the penetration into the artery; and treating a target site using a treatment device.

In another aspect, there is disclosed an arterial access sheath for introducing an interventional device into an artery. The arterial access sheath includes an elongated body sized and shaped to be transcervically introduced into a common carotid artery at an access location in the neck and an internal lumen in the elongated body having a proximal opening in a proximal region of the elongated body and a distal opening in a distal region of the elongated body. The internal lumen provides a passageway for introducing an interventional device into the common carotid artery when the elongated body is positioned in the common carotid artery. The elongated body has a proximal section and a distalmost section that is more flexible than the proximal section. A ratio of an entire length of the distalmost section to an overall length of the sheath body is one tenth to one half the overall length of the sheath body.

Other features and advantages should be apparent from the following description of various embodiments, which illustrate, by way of example, the principles of the invention.

BRIEF DESCRIPTION OF THE DRAWINGS

FIGS. 8-11*b* show embodiments of an arterial access sheath.

DETAILED DESCRIPTION

Disclosed are methods, systems, and devices for accessing and treating the vasculature via a transcarotid access point in the region of the carotid artery.

Figure 1:
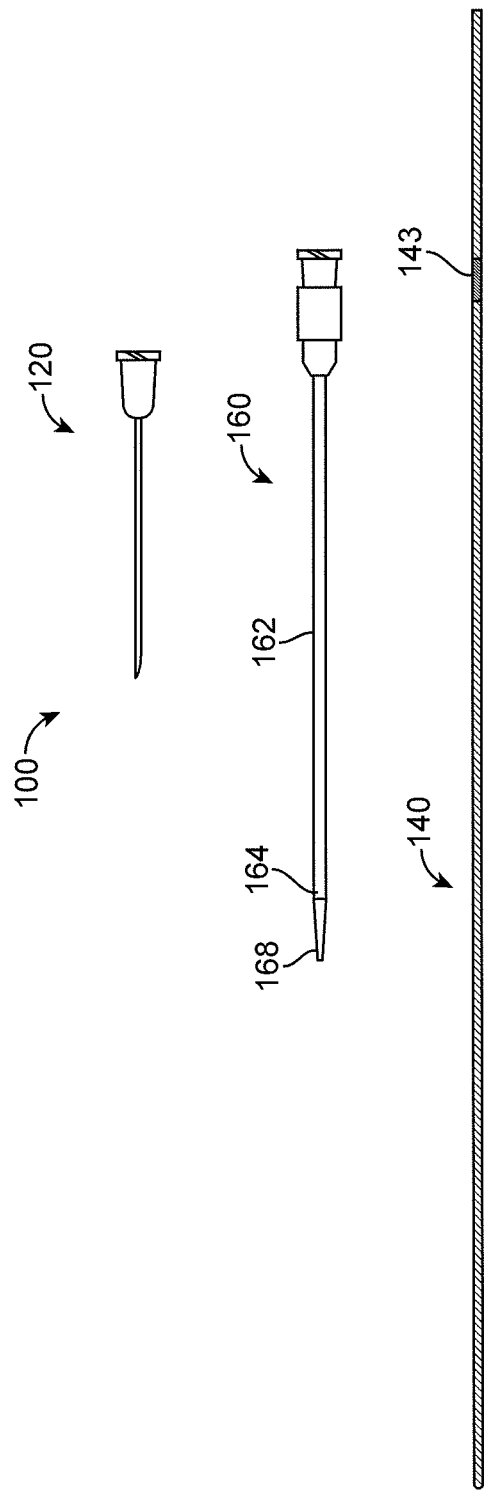
FIG. 1 shows a transcarotid initial access system.

FIG. 1 shows a first embodiment of a transcarotid initial access system 100 of devices for establishing initial access to a carotid artery for the purpose of enabling introduction of a guide wire into the carotid artery. The access to the carotid artery occurs at an access site located in the neck of a patient such as in the region of the patient's carotid artery. The devices of the transcarotid initial access system 100 are particularly suited for directly accessing the carotid artery through the wall of the common carotid artery.

As shown in FIG. 1, the transcarotid initial access system 100 includes an access needle 120, access guidewire 140, and micropuncture cannula 160. The access needle 120, access guidewire 140, and micropuncture cannula 160 are all adapted to be introduced via a carotid puncture into the carotid artery as further described below. The carotid puncture may be accomplished, for example, percutaneously or via a surgical cut down. Embodiments of the initial access system 100 may be adapted towards one or the other method of puncture, as further described below.

Figure 2:
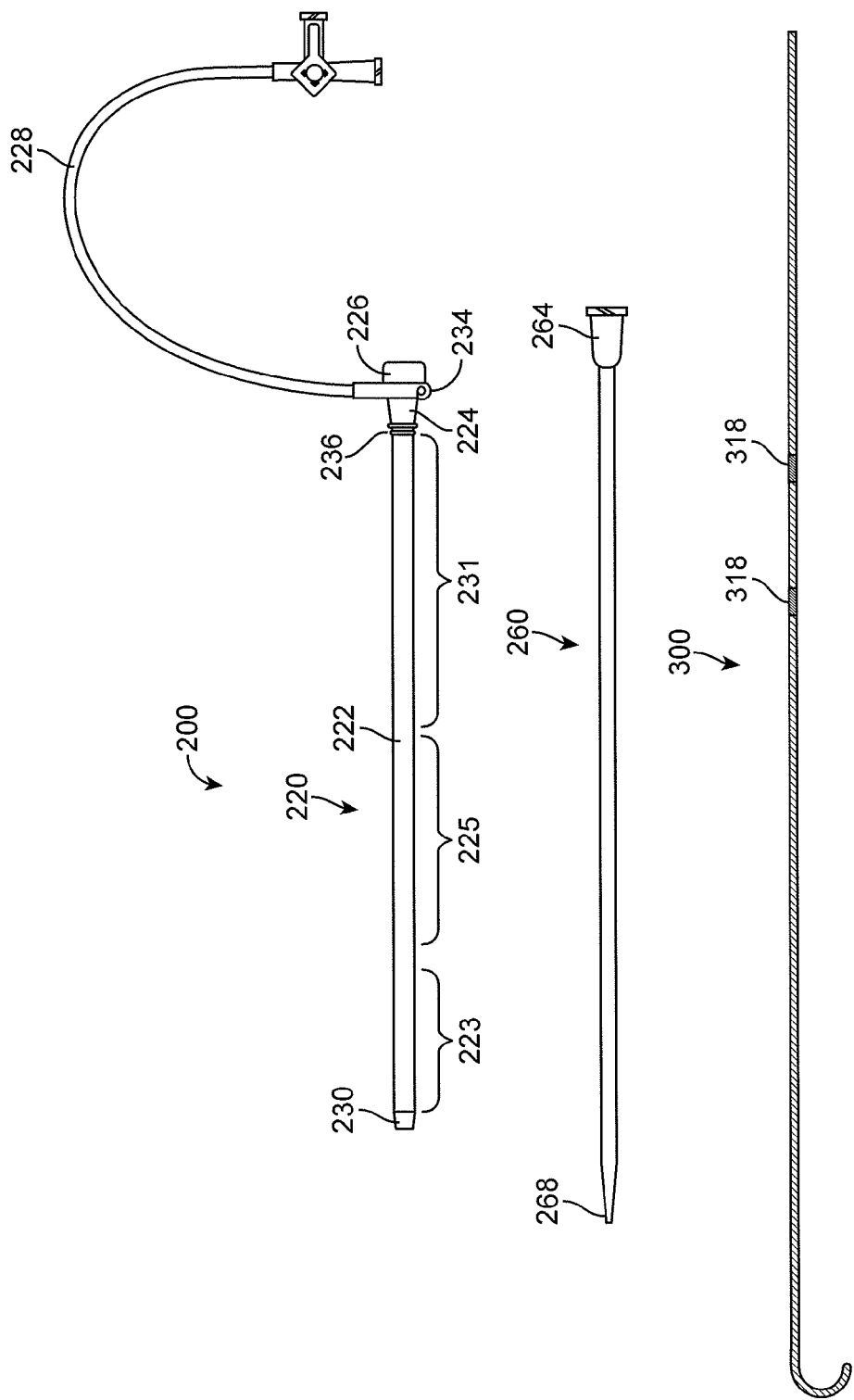
FIG. 2 shows a transcarotid access sheath system.

Upon establishment of access to the carotid artery using the initial access system 100, an access sheath may be inserted into the carotid artery at the access site wherein the access sheath may be part of a transcarotid access sheath system. FIG. 2 shows a first embodiment of a transcarotid access sheath system 200 of devices for inserting an access sheath into the carotid artery over a sheath guidewire. When inserted into the carotid artery, the access sheath enables or allows introduction of at least one interventional device into the carotid artery via a lumen of the access sheath for the purpose of performing an interventional procedure on a region of the vasculature. The transcarotid access sheath system 200 includes an access sheath 220, a sheath dilator 260, and a sheath guidewire 300. The access sheath 220, sheath dilator 260 and sheath guidewire 300 are all adapted to be introduced via a carotid puncture into the carotid artery as further described below. The carotid puncture may be accomplished percutaneously or via a surgical cut down. Embodiments of the system 200 may be adapted towards one or the other method of puncture, as further described below.

In an embodiment, some or all of the components of transcarotid initial access system 100 and the transcarotid access sheath system 200 may be combined into one transcarotid access system kit such as by combining the components into a single, package, container or a collection of containers that are bundled together.

Figure 3:
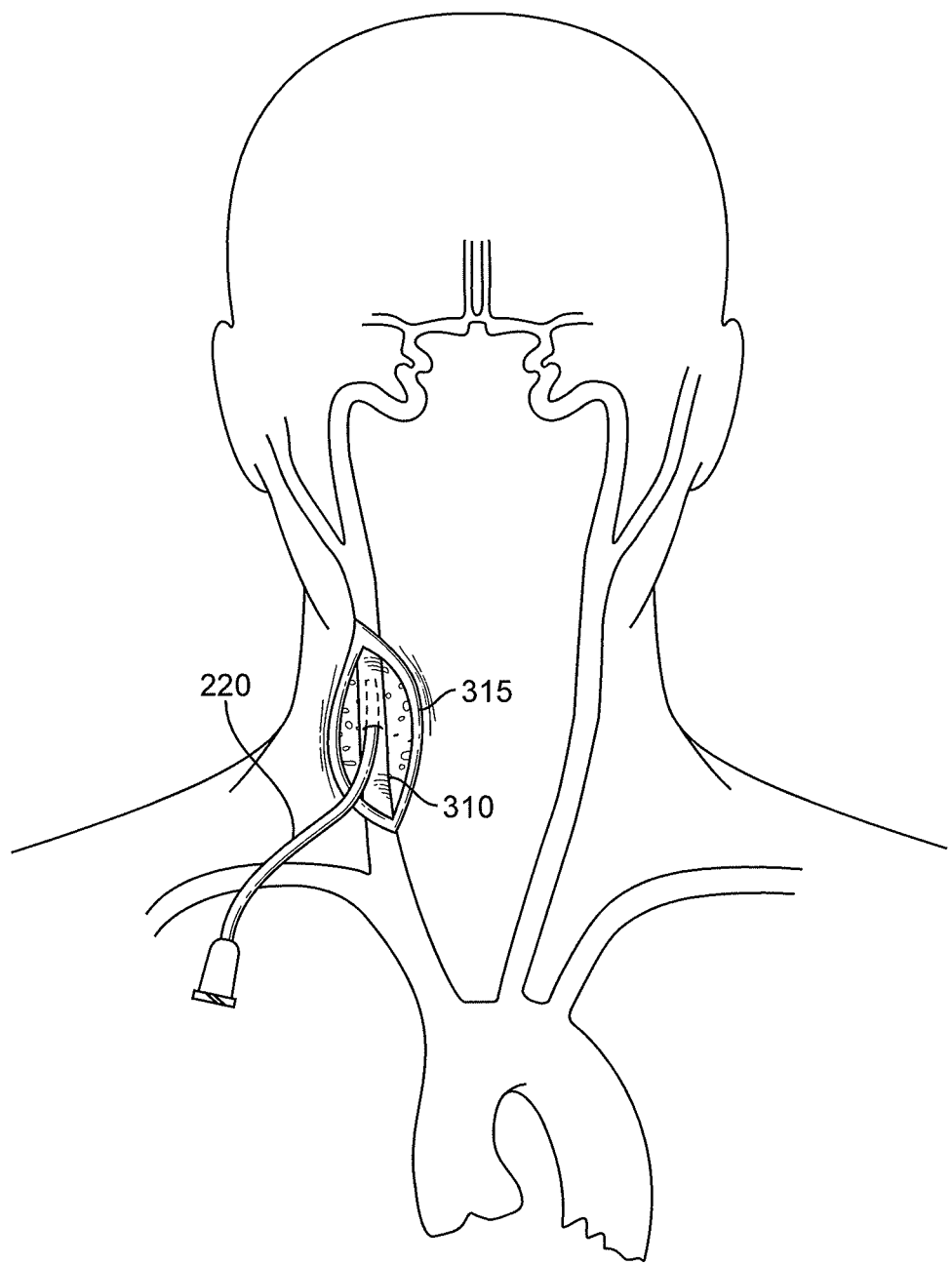
FIG. 3 shows a component of the transcarotid access system being used to access a carotid artery for a carotid artery procedure.

FIG. 3 shows the access sheath 220 being used to access a common carotid artery 310 for a carotid stenting procedure. The access sheath 220 is inserted into the common carotid artery 310 via a surgical cut down 315. As described further below, the access sheath 220 has an internal lumen with openings at proximal and distal tips or regions of the access sheath 220. With a distal portion of the access sheath 220 in the carotid artery and a proximal portion external to the patient, the internal lumen provides a passageway to insert an interventional device into the artery.

Figure 4:
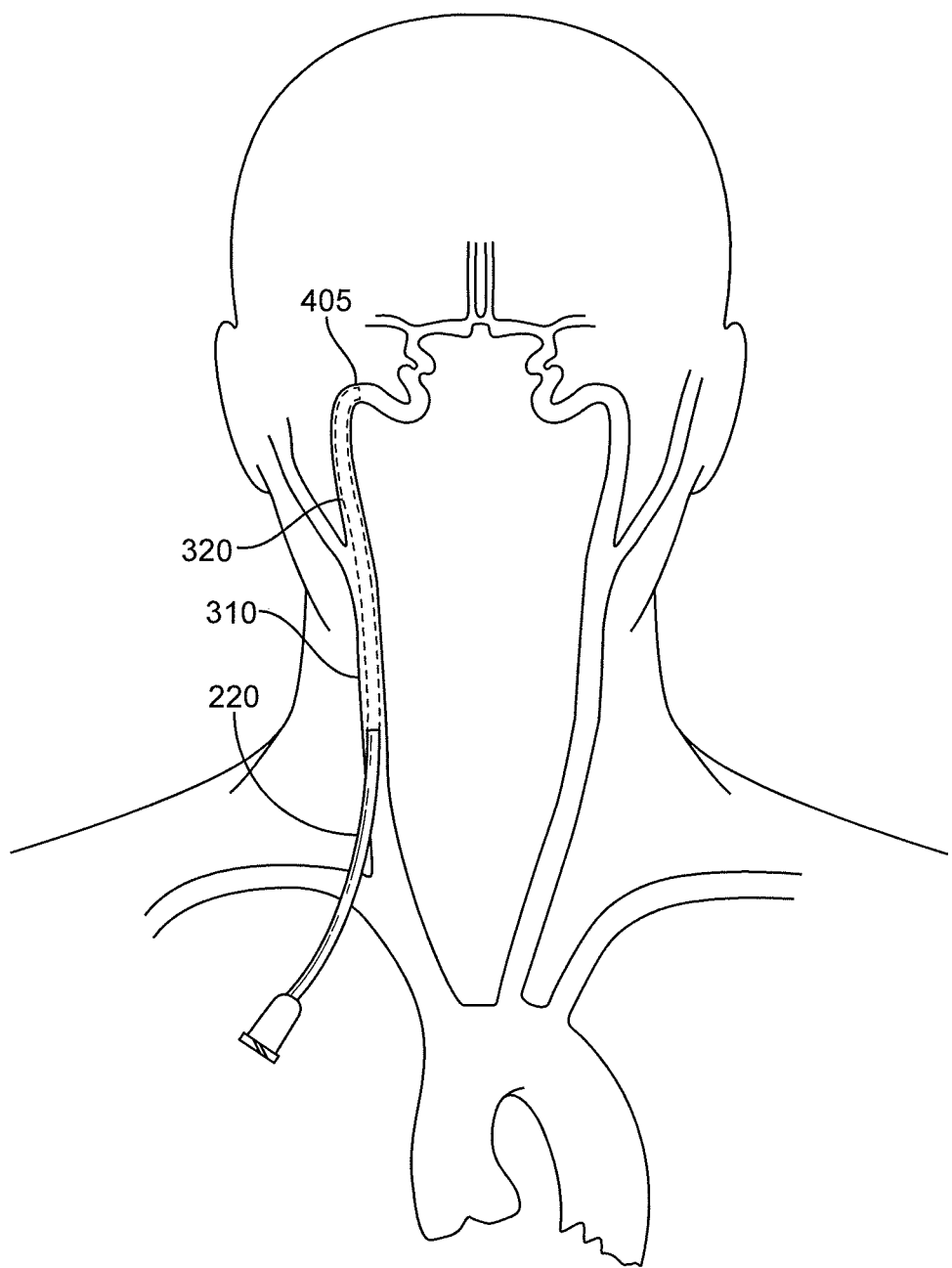
FIG. 4 shows an access sheath of the transcarotid access system being used to access an internal carotid artery for an intracranial or neurovascular procedure.

FIG. 4 shows an access sheath 200 of the transcarotid access system being used to access an internal carotid artery 405 for an intracranial or neurovascular procedure. The arterial access sheath 200 accesses the common carotid artery 310 via insertion through a transcervical puncture. Once inserted into the common carotid artery 310, the distal tip of the access sheath 220 is advanced into the internal carotid artery ICA 320 and upward (relative to the puncture in FIG. 4) toward distal cervical or petrous ICA 405 or beyond.

FIGS. 3 and 4 both show the arterial access sheath 220 being advanced upward through the patient's neck toward the patient's brain. In another embodiment, the arterial access sheath 220 may be advanced downward (relative to access locations in FIGS. 3-4) toward the patient's heart such as toward the aorta for example. U.S. Pat. No. 8,545,552 entitled "Systems and Methods for Transcatheter Aortic Valve Treatment" (which is incorporated herein by reference) describes exemplary methods of directly inserting an access sheath into the carotid artery and advancing an interventional device toward the aorta and ultimately towards the aortic valve.

Arterial Access Sheath

Figure 5:
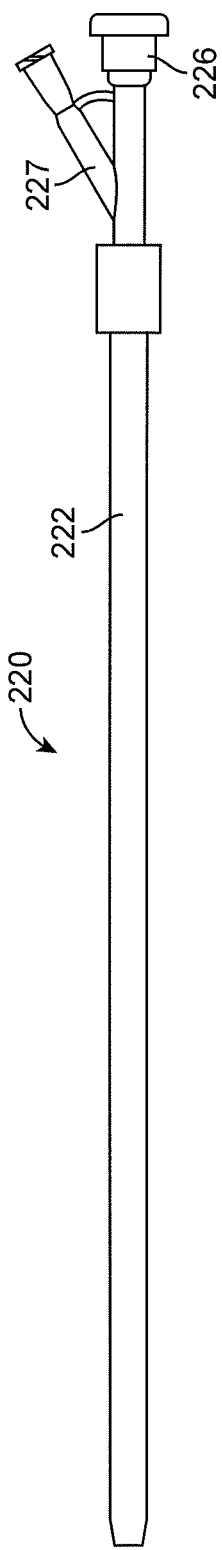
FIG. 5 shows an embodiment of an arterial access sheath.

With reference again to FIG. 2, an embodiment of a transcarotid arterial access sheath 220 includes an elongated sheath body 222 and a proximal adaptor 224 at a proximal end of the elongated sheath body 222 of the access sheath 220. The elongated sheath body 222 is the portion of the arterial access sheath 220 that is sized and shaped to be inserted into the artery and wherein at least a portion of the elongated sheath body is actually inserted into the artery during a procedure. The proximal adaptor 224 includes a hemostasis valve 226 and an elongated flush line 228 having an internal lumen that communicates with an internal lumen of the sheath body 222. The proximal adaptor 224 may have a larger diameter or cross-sectional dimension than the sheath body 222. The hemostasis valve 226 communicates with the internal lumen of the sheath body 222 to allow introduction of devices therein while preventing or minimizing blood loss via the internal lumen during the procedure. In an embodiment, the hemostasis valve 226 is a static seal-type passive valve. In an alternate embodiment of the arterial access sheath 220 (shown in FIG. 5) the hemostasis valve 226 is an adjustable-opening valve such as a Tuohy-Borst valve 227 or rotating hemostasis valve (RHV). Alternately, the access sheath 220 may terminate on the proximal end in a female Luer adaptor to which a separate hemostasis valve component may be attached, either a passive seal valve, a Tuohy-Borst valve or rotating hemostasis valve (RHV).

The elongated sheath body 222 of the arterial access sheath 220 has a diameter that is suitable or particularly optimized to provide arterial access to the carotid artery. In an embodiment, the elongated sheath body 222 is in a size range from 5 to 9 French, or alternately in an inner diameter range from 0.072 inches to 0.126 inches. In an embodiment, the elongated sheath body 222 is a 6 or 7 French sheath. In an embodiment where the sheath is also used for aspiration or reverse flow, or to introduce larger devices, the sheath is an 8 French sheath.

The elongated sheath body 222 of the arterial access sheath 220 has a length from the proximal adapter 224 to a distal tip of the elongated sheath body 222 that is suitable for reaching treatment sites located in or toward the brain relative to an arterial access site in the common carotid artery CCA. For example, to access a carotid artery bifurcation or proximal internal carotid artery ICA from a CCA access site, the elongated sheath body 222 (i.e., the portion that can be inserted into the artery) of the access sheath 220 may have a length in a range from 7 to 15 cm. In an embodiment, the elongated sheath body 222 has a length in the range of 10-12 cm. For access to a same target site from a femoral access site, typical access sheaths must be between 80 and 110 cm, or a guide catheter must be inserted through an arterial access sheath and advanced to the target site. A guide catheter through an access sheath takes up luminal area and thus restricts the size of devices that may be introduced to the target site. Thus an access sheath that allows interventional devices to reach a target site without a guide catheter has advantages over an access sheath that requires use of a guide catheter to allow interventional devices to the target site.

Alternately, to position the distal tip of the elongated sheath body 222 more distally relative to the access site, for example to perform an intracranial or neurovascular procedure from a CCA access site, the elongated sheath body 222 of the access sheath 220 may have a length in the range from 10 cm to 30 cm, depending on the desired target position of the sheath distal tip. For example, if the target position is the distal CCA or proximal ICA, the elongated sheath body 222 may be in the range from 10 cm to 15 cm. If the desired target position is the mid to distal cervical, petrous, or cavernous segments of the ICA, the elongated sheath body 222 may be in the range from 15 to 30 cm.

Alternately, the arterial access sheath 220 is configured or adapted for treatment sites or target locations located proximal to the arterial access site (i.e. towards the aorta) when the access site is in the common carotid artery. For example the treatment site may be the proximal region of the CCA, CCA ostium, ascending or descending aorta or aortic arch, aortic valve, coronary arteries, or other peripheral arteries. For these target locations, the appropriate length of the elongated sheath body 222 depends on the distance from the target location to the access site. In this configuration, the elongated sheath body 222 is placed through an arterial access site and directed inferiorly towards the aorta.

The access sheath 220 may also include a radiopaque tip marker 230. In an example the radiopaque tip marker is a metal band, for example platinum iridium alloy, embedded near the distal end of the sheath body 222 of the access sheath 220. Alternately, the access sheath tip material may be a separate radiopaque material, for example a barium polymer or tungsten polymer blend. The sheath tip itself is configured such that when the access sheath 220 is assembled with the sheath dilator 260 to form a sheath assembly, the sheath assembly can be inserted smoothly over the sheath guide wire 300 through the arterial puncture with minimal resistance. In an embodiment, the elongated sheath body 222 of the access sheath 220 has a lubricious or hydrophilic coating to reduce friction during insertion into the artery. In an embodiment, the distal coating is limited to the distalmost 0.5 to 3 cm of the elongated sheath body 222, so that it facilitates insertion without compromising security of the sheath in the puncture site or the ability of the operator to firmly grasp the sheath during insertion. In an alternate embodiment, the sheath has no coating.

With reference to FIG. 2, in an embodiment, the arterial access sheath 220 has features to aid in securement of the sheath during the procedure. For example the access sheath 220 may have a suture eyelet 234 or one or more ribs 236 molded into or otherwise attached to the adaptor 224 (located at the proximal end of the elongated sheath body 222) which would allow the operator to suture tie the sheath hub to the patient.

For a sheath adapted to be inserted into the common carotid artery for the purpose of access to the carotid bifurcation, the length of the elongated sheath body 222 can be in the range from 7 to 15 cm, usually being from 10 cm to 12 cm. The inner diameter is typically in the range from 5 Fr (1 Fr=0.33 mm), to 10 Fr, usually being 6 to 8 Fr. For a sheath adapted to be inserted via the common carotid artery to the mid or distal internal carotid artery for the purpose of access to the intracranial or cerebral vessels, the length of the elongated sheath body 222 can be in the range from 10 to 30 cm, usually being from 15 cm to 25 cm. The inner diameter is typically in the range from 5 Fr (1 Fr=0.33 mm), to 10 Fr, usually being 5 to 6 Fr.

Particularly when the sheath is being introduced through the transcarotid approach, above the clavicle but below the carotid bifurcation, it is desirable that the elongated sheath body 222 be flexible while retaining hoop strength to resist kinking or buckling. This is especially important in procedures that have limited amount of sheath insertion into the artery, and there is a steep angle of insertion as with a transcarotid access in a patient with a deep carotid artery and/or with a short neck. In these instances, there is a tendency for the sheath body tip to be directed towards the back wall of the artery due to the stiffness of the sheath. This causes a risk of injury from insertion of the sheath body itself, or from devices being inserted through the sheath into the arteries, such as guide wires. Alternately, the distal region of the sheath body may be placed in a distal carotid artery which includes one or more bends, such as the petrous ICA. Thus, it is desirable to construct the sheath body 222 such that it can be flexed when inserted in the artery, while not kinking. In an embodiment, the sheath body 222 is circumferentially reinforced, such as by stainless steel or nitinol braid, helical ribbon, helical wire, cut stainless steel or nitinol hypotube, cut rigid polymer, or the like, and an inner liner so that the reinforcement structure is sandwiched between an outer jacket layer and the inner liner. The inner liner may be a low friction material such as PTFE. The outer jacket may be one or more of a group of materials including Pebax, thermoplastic polyurethane, or nylon.

In an embodiment, the sheath body 222 may vary in flexibility over its length. This change in flexibility may be achieved by various methods. For example, the outer jacket may change in durometer and/or material at various sections. Alternately, the reinforcement structure or the materials may change over the length of the sheath body. In one embodiment, there is a distalmost section of sheath body 222 which is more flexible than the remainder of the sheath body. For example, the flexural stiffness of the distalmost section is one third to one tenth the flexural stiffness of the remainder of the sheath body 222. In an embodiment, the distalmost section has a flexural stiffness (E*I) in the range 50 to 300 N-mm$^2$ and the remaining portion of the sheath body 222 has a flexural stiffness in the range 500 to 1500 N-mm$^2$, where E is the elastic modulus and I is the area moment of inertia of the device. For a sheath configured for a CCA access site, the flexible, distal most section comprises a significant portion of the sheath body 222 which may be expressed as a ratio. In an embodiment, the ratio of length of the flexible, distalmost section to the overall length of the sheath body 222 is at least one tenth and at most one half the length of the entire sheath body 222.

In some instances, the arterial access sheath is configured to access a carotid artery bifurcation or proximal internal carotid artery ICA from a CCA access site. In this instance, an embodiment of the sheath body 222 has a distalmost section 223 which is 3 to 4 cm and the overall sheath body 222 is 10 to 12 cm. In this embodiment, the ratio of length of the flexible, distalmost section to the overall length of the sheath body 222 is about one forth to one half the overall length of the sheath body 222. In another embodiment, there is a transition section 225 between the distalmost flexible section and the proximal section 231, with one or more sections of varying flexibilities between the distalmost section and the remainder of the sheath body. In this embodiment, the distalmost section is 2 to 4 cm, the transition section is 1 to 2 cm and the overall sheath body 222 is 10 to 12 cm, or expressed as a ratio, the distalmost flexible section and the transition section collectively form at least one fourth and at most one half the entire length of the sheath body.

In some instances, the sheath body 222 of the arterial access sheath is configured to be inserted more distally into the internal carotid artery relative to the arterial access location, and possibly into the intracranial section of the internal carotid artery. For example, a distalmost section 223 of the elongated sheath body 222 is 2.5 to 5 cm and the overall sheath body 222 is 20 to 30 cm in length. In this embodiment, the ratio of length of the flexible, distalmost section to the overall length of the sheath body is one tenth to one quarter of the entire sheath body 222. In another embodiment, there is a transition section 225 between the distalmost flexible section and the proximal section 231, in which the distalmost section is 2.5 to 5 cm, the transition section is 2 to 10 cm and the overall sheath body 222 is 20 to 30 cm. In this embodiment, the distalmost flexible section and the transition section collectively form at least one sixth and at most one half the entire length of the sheath body.

Other embodiments are adapted to reduce, minimize or eliminate a risk of injury to the artery caused by the distalmost sheath tip facing and contacting the posterior arterial wall. In some embodiments, the sheath has a structure configured to center the sheath body tip in the lumen of the artery such that the longitudinal axis of the distal region of the sheath body is generally parallel with the longitudinal or center axis of the lumen of the vessel. In an embodiment shown in FIG. 6, the sheath alignment feature is an inflatable or enlargeable bumper, for example a balloon 608, located on an outer wall of the arterial access sheath 220. The balloon 608 may be increased in size to exert a force on inner the arterial that contacts and pushes the elongated body 222 of the aerial access sheath away from the arterial wall.

Figure 6:
FIGS. 6 and 7 show distal regions of an arterial access sheath.

In another embodiment, the sheath alignment feature is one or more mechanical structures on the sheath body that can be actuated to extend outward from the sheath tip. In an embodiment, the sheath body 222 is configured to be inserted into the artery such that a particular edge of the arterial access is against the posterior wall of the artery. In this embodiment, the sheath alignment feature need only extend outward from one direction relative to the longitudinal axis of the sheath body 222 to lift or push the sheath tip away from the posterior arterial wall. For example, as shown in FIG. 6, the inflatable bumper 608 is a blister on one side of the sheath body. In another example, the mechanical feature extends only on one side of the sheath body.

In another embodiment, at least a portion of the sheath body 222 is pre-shaped so that after sheath insertion the tip is more aligned with the long axis of the vessel, even at a steep sheath insertion angle. In this embodiment the sheath body is generally straight when the dilator is assembled with the sheath during sheath insertion over the sheath guide wire, but once the dilator and guidewire are removed, the distalmost section of the sheath body assumes a curved or angled shape. In an embodiment, the sheath body is shaped such that the distalmost 0.5 to 1 cm section is angled from 10 to 30 degrees, as measured from the main axis of the sheath body, with a radius of curvature about 0.5". To retain the curved or angled shape of the sheath body after having been straighten during insertion, the sheath may be heat set in the angled or curved shape during manufacture. Alternately, the reinforcement structure may be constructed out of nitinol and heat shaped into the curved or angled shape during manufacture. Alternately, an additional spring element may be added to the sheath body, for example a strip of spring steel or nitinol, with the correct shape, added to the reinforcement layer of the sheath.

Figure 7:
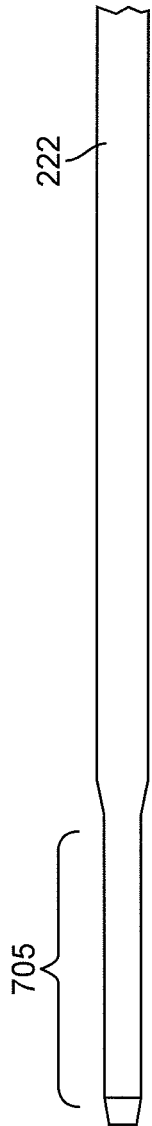

In an alternate embodiment, there are procedures in which it is desirable to minimize flow resistance through the access sheath such as described in U.S. Pat. No. 7,998,104 to Chang and U.S. Pat. No. 8,157,760 to Criado, which are both incorporated by reference herein. FIG. 7 shows such an embodiment of the sheath body 222 where the sheath body has stepped or tapered configuration having a reduced diameter distal region 705 (with the reduced diameter being relative to the remainder of the sheath). The distal region 705 of the stepped sheath can be sized for insertion into the carotid artery, typically having an inner diameter in the range from 0.065 inch to 0.115 inch with the remaining proximal region of the sheath having larger outside and luminal diameters, with the inner diameter typically being in the range from 0.110 inch to 0.135 inch. The larger luminal diameter of the remainder of the sheath body minimizes the overall flow resistance through the sheath. In an embodiment, the reduced-diameter distal section 705 has a length of approximately 2 cm to 4 cm. The relatively short length of the reduced-diameter distal section 705 permits this section to be positioned in the common carotid artery CCA via a transcarotid approach with reduced risk that the distal end of the sheath body will contact the bifurcation B. Moreover, the reduced diameter section also permits a reduction in size of the arteriotomy for introducing the sheath into the artery while having a minimal impact in the level of flow resistance. Further, the reduced distal diameter section may be more flexible and thus more conformal to the lumen of the vessel.

In some instances it is desirable for the sheath body 222 to also be able to occlude the artery in which it is positioned, for examples in procedures that may create distal emboli. In these cases, occluding the artery stops antegrade blood flow in the artery and thereby reduces the risk of distal emboli that may lead to neurologic symptoms such as TIA or stroke. FIG. 8 shows an embodiment of an arterial access sheath 220 with an inflatable balloon 805 on a distal region that is inflated via an inflation line 810 that connect an internal inflation lumen in the sheath body 222 to a stopcock 229 which in turn may be connected to an inflation device. In this embodiment, there is also a Y-arm 815 that may be connected to a passive or active aspiration source to further reduce the risk of distal emboli.

In some instances it is desirable to move the hemostasis valve away from the distal tip of the sheath, while maintaining the length of the insertable sheath body 222 of the sheath. This embodiment is configured to move the hands of the operator, and in fact his or her entire body, away from the target site and therefore from the image intensifier that is used to image the target site fluoroscopically, thus reducing the radiation exposure to the user during the procedure. Essentially, this lengthens the portion of the arterial access sheath 220 that is outside the body. This portion can be a larger inner and outer diameter than the sheath body 222. In instances where the outer diameter of the catheter being inserted into the sheath is close to the inner diameter of the sheath body, the annular space of the lumen that is available for flow is restrictive. Minimizing the sheath body length is thus advantageous to minimize this resistance to flow, such as during flushing of the sheath with saline or contrast solution, or during aspiration or reverse flow out of the sheath. In an embodiment, as shown in FIG. 9, the arterial access sheath 220 has an insertable, elongated sheath body 222 (i.e. the portion configured to insert into the artery) and a proximal extension portion 905. In an embodiment, the sheath body 222 has an inner diameter of about 0.087" and an outer diameter of about 0.104", corresponding to a 6 French sheath size, and the proximal extension has an inner diameter of about 0.100" to 0.125" and an outer diameter of about 0.150" to 0.175". In another embodiment, the sheath body 222 has an inner diameter of about 0.113" and an outer diameter of about 0.136", corresponding to an 8 French sheath size, and the proximal extension has an inner diameter of about 0.125" and an outer diameter of about 0.175". In yet another embodiment, the sheath body 222 is stepped with a smaller diameter distal section 705 to further reduce flow restriction, as in FIG. 7. In an embodiment, the proximal extension 905 is a length suitable to meaningfully reduce the radiation exposure to the user during a transcarotid access procedure. For example, the proximal extension 905 is between 10 and 25 cm, or between 15 and 20 cm. Alternately, the proximal extension 905 has a length configured to provide a distance of between about 30 cm and 60 cm between the hemostasis valve 226 and the distal tip of the sheath body, depending on the insertable length of the access sheath. A connector structure 915 can connect the elongated sheath body 222 to the proximal extension 905. In this embodiment, the connector structure 915 may include a suture eyelet 920 and/or ribs 925 to assist in securing the access sheath to the patient. In an embodiment, the hemostasis valve 226 is a static seal-type passive valve. In an alternate embodiment the hemostasis valve 226 is an adjustable-opening valve such as a Tuohy-Borst valve 227 or rotating hemostasis valve (RHV). Alternately, the proximal extension may terminate on the proximal end in a female Luer adaptor to which a separate hemostasis valve component may be attached, either a passive seal valve, a Tuohy-Borst valve or rotating hemostasis valve (RHV).

Typically, vessel closure devices requires an arterial access sheath with a maximum distance of about 15 cm between distal tip of the sheath body to the proximal aspect of the hemostasis valve, with sheath body 222 of about 11 cm and the remaining 4 cm comprising the length of the proximal hemostasis valve; thus if the access sheath has a distance of greater than 15 cm it is desirable to remove the proximal extension 905 at the end of the procedure. In an embodiment, the proximal extension 905 is removable in such a way that after removal, hemostasis is maintained. For example a hemostasis valve is built into the connector 915 between the sheath body 222 and the proximal extension 905. The hemostasis valve is opened when the proximal extension 905 is attached to allow fluid communication and insertion of devices, but prevents blood flowing out of the sheath when the proximal extension 905 is removed. After the procedure is completed, the proximal extension 905 can be removed, reducing the distance between the proximal aspect of the hemostasis valve and sheath tip from greater than 15 cm to equal or less than 15 cm and thus allowing a vessel closure device to be used with the access sheath 220 to close the access site.

Figure 10:
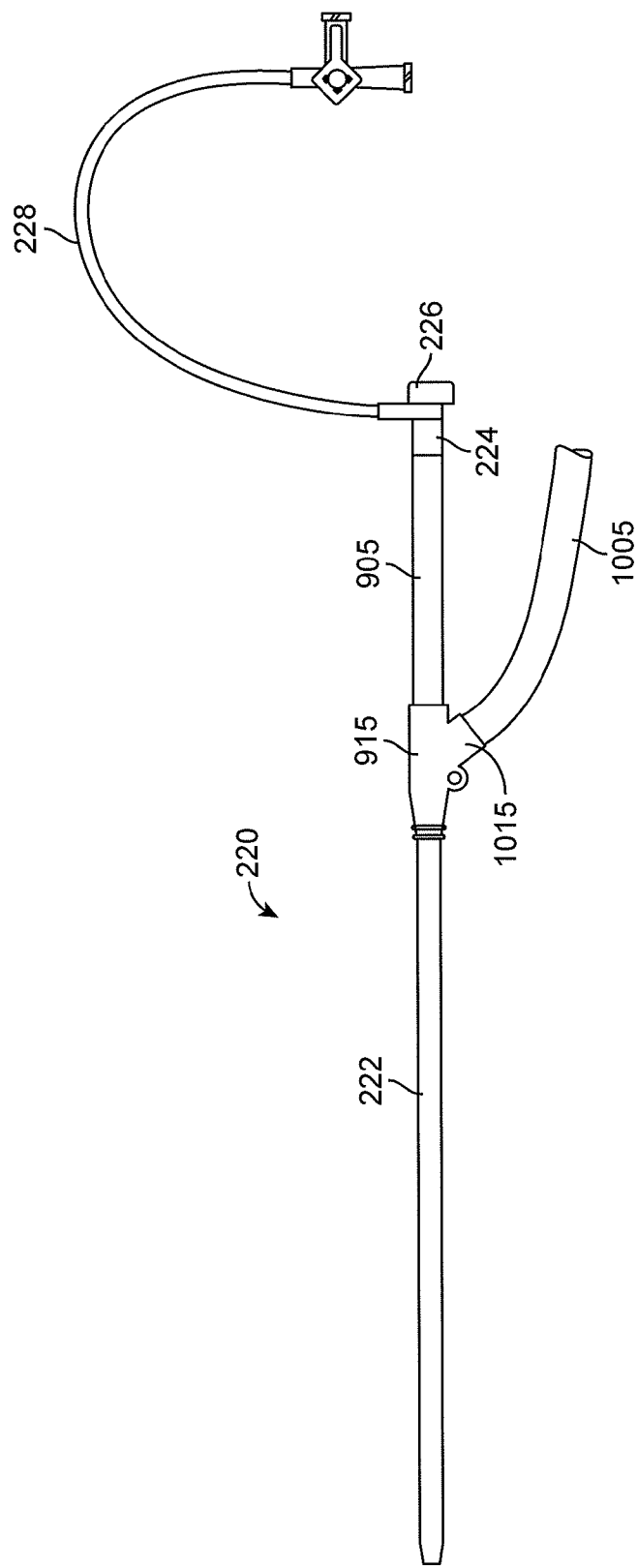

In some procedures it may be desirable to have a low resistance (large bore) flow line or shunt connected to the access sheath, such as described in U.S. Pat. No. 7,998,104 to Chang and U.S. Pat. No. 8,157,760 to Criado, which are both incorporated by reference herein. The arterial sheath embodiment shown in FIG. 10 has a flow line 1005 with internal lumen to a Y-arm 1015 of the connector 915. This flow line has a lumen fluidly connected to a lumen in the sheath body. The flow line 1005 may be connected to a lower pressure return site such as a venous return site or a reservoir. The flow line 1005 may also be connected to an aspiration source such as a pump or a syringe. In an embodiment, an occlusion element may also be included on the distal end of the sheath body 222, for example an occlusion balloon. This may be desirable in percutaneous procedures, where the vessel cannot be occluded by vascular surgical means such as vessel loops or vascular clamps.

In some procedures, it may be desirable to limit the amount of sheath body insertion into the artery, for example in procedures where the target area is very close to the arterial access site. In a stent procedure of the carotid artery bifurcation, for example, the sheath tip should be positioned proximal of the treatment site (relative to the access location) so that it does not interfere with stent deployment or enter the diseased area and possibly cause emboli to get knocked loose. In an embodiment of arterial sheath 220 shown in FIGS. 11A and 11B, a sheath stopper 1105 is slideably connected or mounted over the outside of the distal portion of the sheath body. The sheath stopper 1105 is shorter than the distal portion of the sheath, effectively shortening the insertable portion of the sheath body 222 by creating a positive stop at a certain length along the sheath body 222. The sheath stopper 1105 may be a tube that slidably fits over the sheath body 222 with a length that, when positioned on the sheath body 222, leaves a distal portion of the sheath body exposed. This length can be in the range 2 to 4 cm. More particularly, the length is 2.5 cm. The distal end of the sheath stopper 1105 may be angled and oriented such that the angle sits flush with the vessel and serves as a stop against the arterial wall when the sheath is inserted into the artery when the vessel is inserted into the artery, as shown in FIG. 11A. Alternately, the distal end of the sheath stopper may be formed into an angled flange 1115 that contacts the arterial wall, as shown in FIG. 11B. The flange 1115 is rounded or has an atraumatic shape to create a more positive and atraumatic stop against the arterial wall. The sheath stopper 1105 may be permanently secured to the arterial sheath, for example the proximal end of the sheath stopper may be adhered to connector 915 of the arterial access sheath. Alternately, the sheath stopper 1105 may be removable from the arterial access sheath 220 by the user so it can be optionally utilized in a procedure. In this instance, the sheath stopper 1105 may have a locking feature on the proximal portion that engages with a corresponding locking features on the connector 915, for example slots or recesses on the proximal sheath stopper engaging protrusions on the connector. Other locking features may also be utilized.

In situations where the insertion of the sheath body is limited to between 2 and 3 cm, and particularly when the sheath body is inserted at a steep angle, the sheath may conform to a bayonet shape when secured to the patient. For example, the bayonet shape may comprise a first portion that extends along a first axis and a second portion that extends along a second axis that is axially offset from the first axis and/or non-parallel to the first axis. The springiness of the sheath body causes this shape to exert a force on the vessel at the site of insertion and increase the tendency of the sheath to come out of the vessel if not properly secured. To reduce the stress on the vessel, the sheath stopper may be pre-shaped into a curved or bayonet shape so that the stress of the sheath body when curved is imparted onto the sheath stopper rather than on the vessel. The sheath stopper may be made from springy but bendable material or include a spring element such as a stainless steel or nitinol wire or strip, so that when the dilator is inserted into the sheath and sheath stopper assembly, the sheath is relatively straight, but when the dilator is removed the sheath stopper assumes the pre-curved shape to reduce the force the sheath imparts on the vessel wall. Alternately, the sheath stopper may be made of malleable material or include a malleable element such as a bendable metal wire or strip, so that it can be shaped after the sheath is inserted into a desired curvature, again to reduce the stress the sheath imparts on the vessel wall.

Sheath Dilator

With reference again to FIG. 2, the sheath dilator 260 is a component of the transcarotid access sheath system 200. The sheath dilator 260 is an elongated body that is inserted into the artery and enables smooth insertion of the access sheath 220 over the sheath guidewire 300 through a puncture site in the arterial wall. Thus, the distal end of the dilator 260 is generally tapered to allow the dilator to be inserted over the sheath guidewire 300 into the artery, and to dilate the needle puncture site to a larger diameter for insertion of the access sheath 220 itself. To accommodate these functions, the dilator 260 has a tapered end 268 with a taper that is generally between 6 and 12 degrees total included angle (relative to a longitudinal axis of the dilator), with a radiused leading edge. Sheath dilators are typically locked to the access sheath when assembled for insertion into the artery. For example a proximal hub 264 of the sheath dilator 260 is structured to snap into or over a corresponding structure on the hemostasis valve 226 of the arterial access sheath 220. An inner lumen of the dilator 260 accommodates a sheath guidewire 300, with an inner diameter of between 0.037 to 0.041", depending on the sheath guide wire size for example.

For a transcarotid access sheath system 200, it may be desirable to make the distal section of the sheath dilator 260 more flexible, to correspond with an increased flexible section of the access sheath 220. For example, the distal 2 to 5 cm of the sheath dilator 260 may be 20 to 50% more flexible than the proximal portion of the sheath dilator 260. This embodiment would allow a sheath and dilator being inserted to accommodate a steep insertion angle, as is often the case in a transcarotid access procedure, with a smoother insertion over the guidewire while still maintaining columnar support of the dilator. The columnar support is desirable to provide the insertion force required to dilate the puncture site and insert the access sheath.

For some transcarotid access sheath systems, it may be desirable to also use a smaller diameter access guidewire (for example in the range 0.014" to 0.018" diameter) to guide the sheath and dilator into the artery. In this embodiment, the sheath dilator tapered end 268 is configured to provide a smooth transition from a smaller wire size to the access sheath. In one variation, the sheath guide wire is 0.018" and the inner dilator lumen is in the range 0.020"-0.022". In another variation, the sheath guide wire is 0.014" and the inner dilator lumen is in the range 0.016" to 0.018". The taper is similarly modified, for example the taper length is longer to accommodate a taper from a smaller diameter to the inner diameter of the access sheath, or may comprise two taper angles to provide a smooth transition from the smaller diameter wire to the access sheath without overly lengthening the overall length of the taper.

In some procedures, it is desirable to position the distal tip of the sheath body 222 of the arterial access sheath 220 in the mid to distal cervical, petrous, or cavernous segments of the ICA as described above. These segments have curvature often greater than 90 degrees. In may be desirable to have a sheath dilator with a softer and longer taper, to be able to navigate these bends easily without risk of injury to the arteries. However, in order to insert the sheath through the arterial puncture, the dilator desirably has a certain stiffness and taper to provide the dilating force. In an embodiment, the transcarotid access sheath system 200 is supplied or included in a kit that includes two or more tapered dilators 260A and 260B. The first tapered dilator 260A is used with the arterial access device to gain entry into the artery, and is thus sized and constructed in a manner similar to standard introducer sheath dilators. Example materials that may be used for the tapered dilator include, for example, high density polyethylene, 72D Pebax, 90D Pebax, or equivalent stiffness and lubricity material. A second tapered dilator 260B of the kit may be supplied with the arterial access device with a softer distal section or a distal section that has a lower bending stiffness relative to the distal section of the first tapered dilator. That is, the second dilator has a distal region that is softer, more flexible, or articulates or bends more easily than a corresponding distal region of the first dilator. The distal region of the second dilator thus bends more easily than the corresponding distal region of the first dilator. In an embodiment, the distal section of the first dilator 260A has a bending stiffness in the range of 50 to 100 N-mm$^2$ and the distal section of the second dilator 260B has a bending stiffness in the range of 5 to 15 N-mm$^2$.

The second dilator 260B (which has a distal section with a lower bending stiffness) may be exchanged with the initial, first dilator such that the arterial access device may be inserted into the internal carotid artery and around curvature in the artery without undue force or trauma on the vessel due to the softer distal section of the second dilator. The distal section of the soft, second dilator may be, for example, 35 or 40D Pebax, with a proximal portion made of, for example 72D Pebax. An intermediate mid portion or portions may be included on the second dilator to provide a smooth transition between the soft distal section and the stiffer proximal section. In an embodiment, one or both dilators may have radiopaque tip markers so that the dilator tip position is visible on fluoroscopy. In one variation, the radiopaque marker is a section of tungsten loaded Pebax or polyurethane which is heat welded to the distal tip of the dilator. Other radiopaque materials may similarly be used to create a radiopaque marker at the distal tip.

Figure 12:
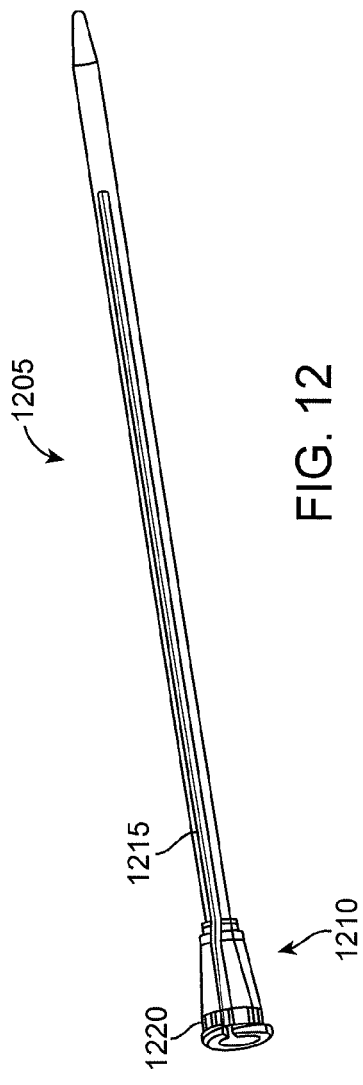
FIG. 12 shows an embodiment of a dilator.

To facilitate exchange of the first dilator for the second dilator, one or both dilators may be configured such that the distal section of the dilator is constructed from a tapered single-lumen tube, but the proximal portion of the dilator and any adaptor on the proximal end has a side opening. FIG. 12 shows an example of a dilator 1205 formed of an elongated member sized and shaped to be inserted into an artery, and a proximal hub 1210. The dilator has a side opening 1215, such as a slot, that extends along at least a portion of the length of the dilator 1205 such as along the elongated body and the proximal hub 1210. In an embodiment, the side opening 1215 is located only on a proximal region of the dilator 1205 and through the proximal hub 1210 although this may vary. The side opening 1215 provides access to an internal lumen of the dilator 1205, such as to insert and/or remove a guidewire into or from the lumen. An annular, movable sleeve 1220 with a slot on one side is located at or near the proximal hub 1210 of the dilator 1205. The sleeve 1220 may be moved, such as via rotation, about a longitudinal axis of the hub 1210, as described below. Note that the distal end of the dilator 1205 has a tapered configuration for dilating tissue.

Figure 14:
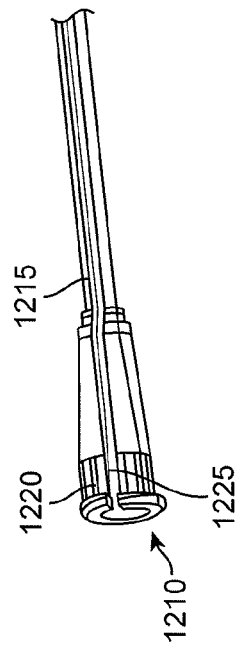
FIGS. 13 and 14 show enlarged views of the proximal region of the dilator.
Figure 13:
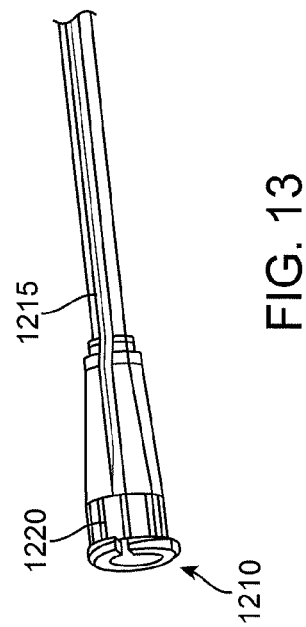

FIG. 13 shows an enlarged view of the proximal region of the dilator 1205. As mentioned, the dilator 1205 has a side opening 1215 in the form of a slot that extends along the length of the dilator 1205 and the proximal hub 1210. The sleeve 1220 is positioned around the outer periphery of the dilator and is shaped such that it covers at least a portion of the side opening 1215. Thus, the sleeve 1220 can prevent a guidewire positioned inside the dilator 1205 from exiting the dilator via the side opening 1215. As mentioned, the sleeve 1220 is rotatable relative to the dilator 1205 and proximal hub 1210. In the illustrated embodiment, the sleeve 1220 is rotatable about a longitudinal axis of the dilator 1205 although other types of relative movement are within the scope of this disclosure. As shown in FIG. 14, the sleeve 1220 has a slot 1225 that can be aligned with the side opening 1215. When aligned as such, the slot 1225 and side opening 1215 collectively provide an opening for a guidewire to be inserted or removed from the internal lumen of the dilator 1205. The sleeve 1220 can be rotated between the position shown in FIG. 13 (where it covers the side opening 1215) and the position shown in FIG. 14 (where the side opening is uncovered due to the slot 1225 being aligned with the side opening 1215.)

A method of use of this embodiment of an access sheath kit is now described. A sheath guide wire, such as an 0.035" guidewire, is inserted into the common carotid artery, either using a Modified Seldinger technique or a micropuncture technique. The distal end of the guidewire can be positioned into the internal or external carotid artery, or stop in the common carotid artery short of the bifurcation. The arterial access sheath with the first, stiffer dilator, is inserted over the 0.035" wire into the artery. The arterial access sheath is inserted such that at least 2.5 cm of sheath body 222 is in the artery. If additional purchase is desired, the arterial access sheath may be directed further, and into the internal carotid artery. The first dilator is removed while keeping both the arterial access sheath and the 0.035" wire in place. The side opening 1215 in the proximal portion of the dilator allows the dilator to be removed in a "rapid exchange" fashion such that most of the guidewire outside the access device may be grasped directly during dilator removal. The second dilator is then loaded on to the 0.035" wire and inserted into the sheath. Again, a dilator with a side opening 1215 in the proximal portion of the dilator may be used to allow the 0.035" wire to be grasped directly during guide wire insertion in a "rapid exchange" technique. Once the second dilator is fully inserted into the arterial access device, the arterial access sheath with the softer tipped, second dilator is advanced up the internal carotid artery and around bends in the artery without undue force or concern for vessel trauma. This configuration allows a more distal placement of the arterial access sheath without compromising the ability of the device to be inserted into the artery.

Alternately, one or more standard dilators may be used without side openings. If a standard dilator without a side opening is used, after the access device is inserted into the artery over a guide wire with the first dilator, the first dilator may be removed together with the guidewire, leaving only the access device in place. The second dilator with a guide wire preloaded into the central lumen may be inserted together into the arterial access device. Once fully inserted, the access device and second dilator with softer tip may be advanced distally up the internal carotid artery as above. In this alternate method, the initial guide wire may be used with both dilators, or may be exchanged for a softer tipped guide wire when inserted with the second softer tipped dilator.

In some instances, it may be desirable to insert the access sheath system over an 0.035" wire into the carotid artery, but then exchange the wire to a smaller guidewire, in the range 0.014" to 0.018". Because the access into the carotid artery may require a steep angle of entry, a wire that can offer good support such as an 0.035" wire may be desirable to initially introduce the access sheath into the CCA. However, once the sheath is in the artery but the user would like to advance it further over a smaller guidewire, it may be desirable to exchange the 0.035" wire for a smaller guide wire. Alternately, the user may exchange both the dilator and 0.035" wire for a softer dilator and smaller guide wire in the range 0.014" to 0.018". Alternately, the user may wish to position an 0.014" guidewire which he or she will subsequently to introduce an interventional device, while the sheath and dilator are still in place. The dilator may offer access and support for this guide wire, and in instances of severe access sheath angle may aid in directing the wire away from the posterior wall of the artery so that the wire may be safely advanced into the vascular lumen without risk of luminal injury.

Figure 15:
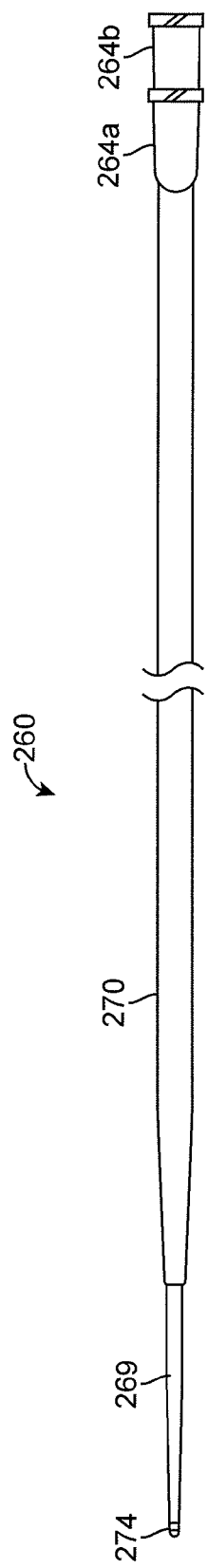
FIGS. 15 and 16 show embodiments of a two part dilator.
Figure 16:
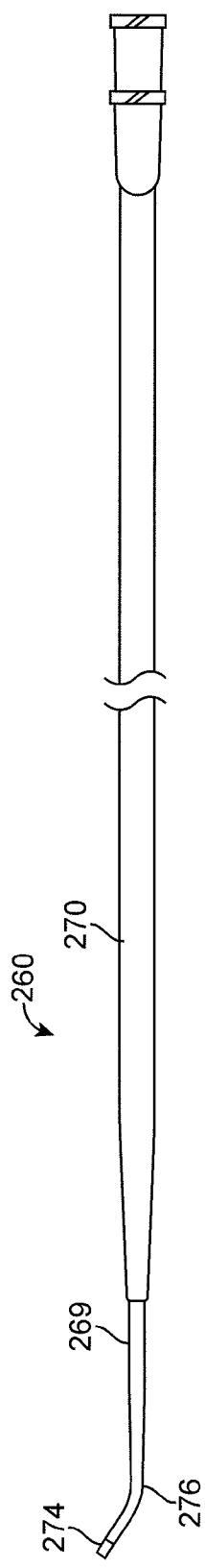

In an embodiment as shown in FIG. 15, the sheath dilator 260 is a two-part dilator assembly, with an inner dilator 269 and an outer dilator 270 that slidably attach to one another in a co-axial arrangement. Both dilators have proximal hubs 264a and 264b. When the two dilators are assembled together, the two hubs 264a and 264b have features which allow them to be locked together, e.g. a snap fit or a threaded fit, so that the two dilators can be handled as one unit. In an embodiment, the inner dilator 269 has a proximal hub 264b which includes a rotating coupler with internal threads that engage external threads on the proximal hub 264a of the outer dilator 270. The inner dilator 269 effectively transforms the dilator assembly from an 0.035" or 0.038" wire compatible dilator to an 0.018" or 0.014" wire compatible dilator, and extends out the distal end of the outer dilator. In an embodiment, shown in FIG. 16, the inner dilator has an angled tip 276 that is bent or angled relative to a longitudinal axis of the remainder of the dilator. In an embodiment, the angle is a 45 degree angle. This angled tip 276 allows the user to direct the guidewire into one or another branch vessel more easily. The inner dilator may have a tapered tip, straight as shown in FIG. 15 or an angled tip as shown in FIG. 16. Alternately, the inner dilator may have a constant outer diameter to the distal end, with a rounded leading edge. In an embodiment, the inner dilator has a radiopaque marker 274 at or near the distal tip to aid in visualization of the dilator under fluoroscopy. In an embodiment, the inner dilator is reinforced to make it more torquable to aid in directing the angled tip in a particular direction. For example the dilator may have a coil or braid reinforcement layer. Once the interventional wire is positioned, the two-part dilator is removed and the wire may then be used to insert interventional devices through the arterial sheath into the artery and advanced to the treatment site.

Figure 17:
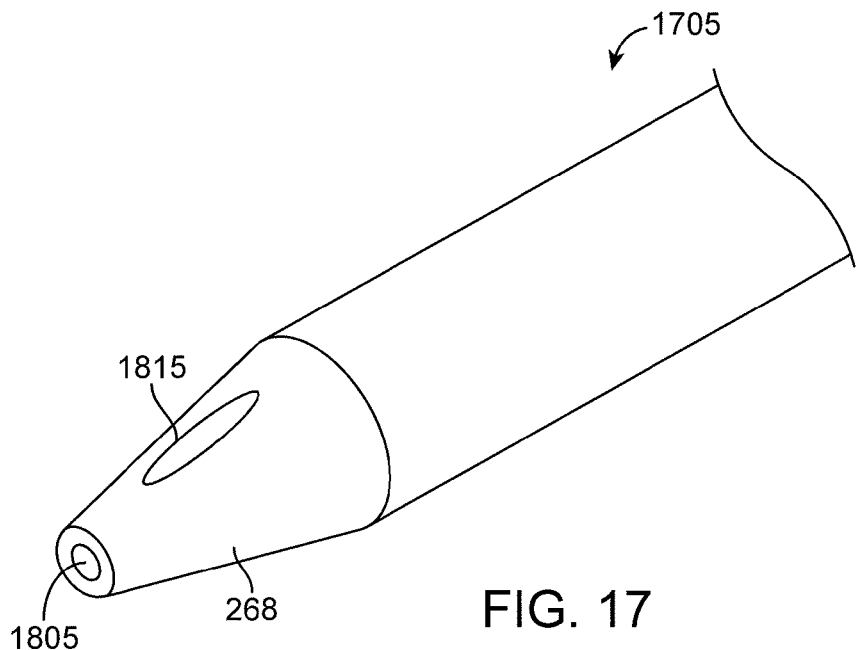
FIG. 17 shows a distal region of a dilator having two guidewire lumens.
Figure 18:
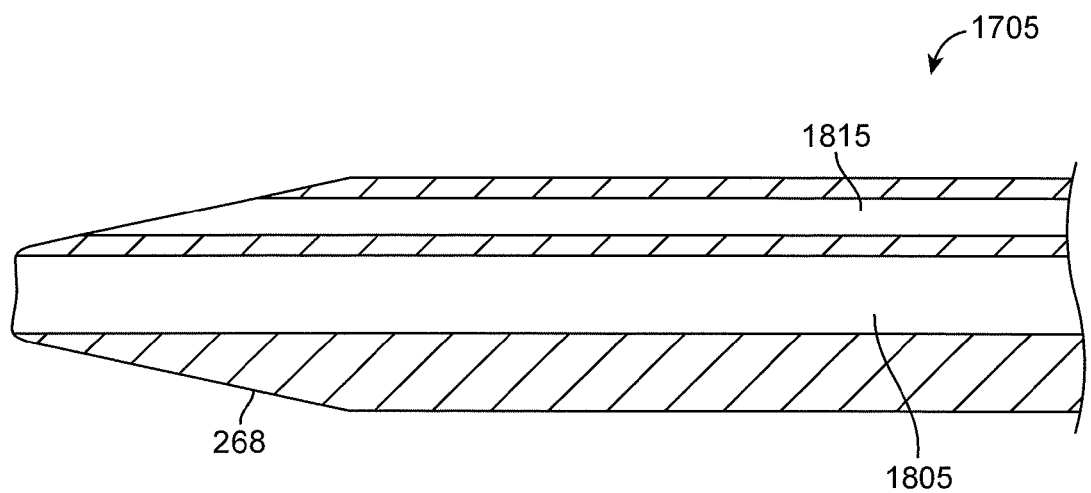
FIG. 18 shows a cross-sectional view of the distal region of FIG. 17.

An alternate embodiment, shown in FIG. 17, allows two separate wire sizes to be used with the dilator. This embodiment includes a dilator 1705 with two guide wire internal lumens that extend along the length of the device. FIG. 17 shows the distal end of this embodiment. As seen more clearly in a cross sectional view FIG. 18, one lumen 1805 is configured for an 0.035" or 0.038" guidewire, and the other lumen 1815 is for a an 0.014" to 0.018" guide wire. In this embodiment, the larger lumen 1805 is centered around the centerline of the taper 268, whereas the smaller lumen 1815 is offset from the centerline of the taper. In this configuration, the access sheath is introduced into the artery over the larger guidewire, which is positioned in the larger lumen 1805. Once positioned, an interventional wire can be placed through the second lumen 1815. The larger guidewire and dilator are then removed from the access sheath and the interventional wire may then be used to insert interventional devices through the arterial sheath into the artery and advanced to the treatment site as above.

Sheath Guidewire

Arterial access sheaths are typically introduced into the artery over a sheath guidewire of 0.035" or 0.038" diameter. The inner diameter and taper length of the distal tip of the dilator are sized to fit with such a guidewire. Some sheaths, for example for radial artery access, are sized to accommodate a sheath guidewire of 0.018" diameter, with a corresponding dilator having a distal tip inner diameter and taper length. The sheath guidewire may have an atraumatic straight, angled, or J-tip. The guidewire smoothly transitions to a stiffer segment on the proximal end. This configuration allows atraumatic entry and advancement of the wire into the artery while allowing support for the sheath when the sheath is introduced into the artery over the wire. Typically the transition from the atraumatic tip is about 4 to 9 cm to the stiffer section. The sheath is usually inserted 15 to 20 cm into the artery, so that the stiffer segment of the wire is at the arterial entry site when the sheath is being inserted.

However, in the case of a transcarotid access entry point, the amount of wire that can be inserted is much less than 15 cm before potentially causing harm to the distal vessels. In a case of a transcarotid access for a carotid stent or PTA procedure, it is very important that the wire insertion length is limited, to avoid risk of distal emboli being generated by the sheath guide wire at the site of carotid artery disease. Thus it is desirable to provide a guide wire that is able to provide support for a potentially steep sheath entry angle while being limited in length of insertion. In an embodiment, a transcarotid sheath guidewire has an atraumatic tip section but have a very distal and short transition to a stiffer section. For example, the soft tip section is 1.5 to 2.5 cm, followed by a transition section with length from 3 to 5 cm, followed by a stiffer proximal segment, with the stiffer proximal section comprising the remainder of the wire.

The sheath guidewire may have guide wire markings 318 to help the user determine where the tip of the wire is with respect to the dilator. For example, there may be a marking on the proximal end of the wire corresponding to when the tip of the wire is about to exit the micro access cannula tip. This marking would provide rapid wire position feedback to help the user limit the amount of wire insertion. In another embodiment, the wire may include an additional mark to let the user know the wire has existed the cannula by a set distance, for example 5 cm.

Micro Access Components

With reference to FIG. 1, a micro access kit 100 for initial transcarotid access includes an access needle 120, an access guidewire 140, and a micro access cannula 160. The micro access cannula 160 includes a body 162 and an inner dilator 168 slidably positioned within a lumen of the body 162. Typically for arterial access, the initial needle puncture may be with a 21G or 22G access needle, or an 18G needle if the Modified Seldinger technique is used. For transcarotid access, it may be desirable to access with an even smaller needle puncture. Percutaneous access of the carotid artery is typically more challenging than of the femoral artery. The carotid artery is a thicker-walled artery, it is surrounded by a tissue sleeve known as the carotid sheath, and it is not anchored down as much by surrounding musculature, therefore the initial needle stick is more difficult and must be done with more force, onto an artery that is less stable, thus increasing the risk of mis-placed puncture, arterial dissection, or back wall puncture. A smaller initial needle puncture, for example a 23G or 24G needle, increases the ease of needle entry and reduce these risks. The sheath guidewire should be accordingly sized to fit into the smaller needle, for example a 0.016" or 0.014" wire. The access needle 120 may include a textured surface on the distal end to render it visible on ultrasound, to aid in ultrasound-guided insertion of the needle into the artery. The needle length may be in a range from 4 cm to 8 cm in length.

Similarly to sheath guide wires, micro access guide wires have a transition segment from a floppy distal tip to a core section that is stiffer than the distal tip or distal region. Such micro access guidewires are typically 0.018" in diameter, with a floppy, distal segment of about 1-2 cm, and a transition zone of 5-6 cm to the stiffer segment. In an embodiment, a transcarotid access guidewire is from 0.014" to 0.018" in diameter, and has a floppy segment of 1 cm, a transition zone of 2-3 cm to bring the stiff supportive section much closer to the distal tip. This will allow the user to have good support for his micro access cannula insertion even in steep access angles and limitations on wire insertion length.

As with the sheath guide wire, the micro access guide wire may have guide wire markings 143 to help the user determine where the tip of the wire is with respect to the micro cannula. For example, a marking can be located on the proximal end of the wire corresponding to when the tip of the wire is about to exit the micro cannula. This marking would provide rapid wire position feedback to help the user limit the amount of wire insertion. In another embodiment, the wire may include an additional mark to let the user know the wire has existed the dilator by a set distance, for example 5 cm.

The micro access cannula itself may be configured for transcarotid insertion. Typically, the micro access cannula 160 includes a cannula 162 and an inner dilator 168 with a tapered tip. The inner dilator 168 provides a smooth transition between the cannula and the access guide wire. The cannula is sized to receive the 0.035" wire, with inner diameter in the range 0.038" to 0.042". In an embodiment, a micro access cannula 160 is configured for transcarotid access. For example the dilator of the cannula may be sized for a smaller 0.014" access guide wire 140. Additionally, the cannula itself may have depth marking to aid the user in limiting the amount of insertion. In an embodiment, the micro access cannula 160 has a radiopaque marker 164 at the distal tip of the cannula 162 to help the user visualize the tip location under fluoroscopy. This is useful for example in cases where the user may want to position the cannula in the ICA or ECA, for example.

Exemplary Kits:

Any or all of the devices described above may be provided in kit form to the user such that one or more of the components of the systems are included in a common package or collection of packages. An embodiment of an access sheath kit comprises an access sheath, sheath dilator, and sheath guidewire all configured for transcarotid access as described above.

In an embodiment, a micro access kit comprises an access needle, a micro access guide wire, and a micro access cannula and dilator wherein the guidewire is 0.014" and the micro access cannula and dilator are sized to be compatible with the 0.014" guide wire.

In an embodiment, an access kit comprises the access sheath, sheath dilator, sheath guide wire, access needle, micro access guide wire and micro access cannula and dilator, all configured for transcarotid access.

In an alternate embodiment, the access guidewire is also used as the sheath guide wire. In this embodiment, the access kit comprises an access needle, access guide wire, access sheath and dilator. The sheath and dilator use the access guide wire to be inserted into the vessel, thereby avoiding the steps required to exchange up to a larger sheath guidewire. In this embodiment, the dilator taper length and inner lumen is sized to be compatible with the smaller access guide wire. In one embodiment the access guide wire is 0.018". In an alternate embodiment the access guide wire is 0.016". In an alternate embodiment, the access guide wire is 0.014".

Exemplary Methods:

There are now described exemplary methods of use for a transcarotid access system. In an exemplary transcarotid procedure to treat a carotid artery stenosis, the user starts by performing a cut down to the common carotid artery. The user then inserts an access needle 120 into the common carotid artery at the desired access site. An access guide wire 140 with a taper configured for transcarotid access is inserted through the needle into the common carotid artery and advanced into the CCA. The access needle 120 is removed and a micro access cannula 160 is inserted over the wire 140 into the CCA. The micro access cannula is inserted a desired depth using the marks 166 on the cannula as a guide, to prevent over insertion.

The user removes the cannula inner dilator 168 and guide wire 140, leaving the cannula 162 in place. If desired, the user performs an angiogram through the cannula 162. The user then places sheath guide wire 300 through the cannula, using guide wire markings 318 to aid in inserting the wire to a desired insertion length. The cannula 162 is removed from the guidewire and the access sheath 220 and sheath dilator 260 are inserted as an assembly over the sheath guidewire 300 into the CCA. The sheath stopper flange 1115 of the sheath stopper 1105 limits the insertion length of the arterial sheath. Once positioned, the dilator 260 and guidewire 300 are removed. The sheath is then sutured to the patient using the securing eyelets 234 and/or ribs 236. An interventional procedure is then performed by introduction of interventional devices through hemostasis valve 226 on the proximal end of the arterial sheath and to the desire treatment site. Contrast injections may be made as desired during the procedure via the flush arm 228 on the arterial sheath 220.

Alternately, the sheath guidewire 300 is placed into the CCA via a single needle puncture with a larger access needle, for example an 18G needle. In this embodiment, the access cannula and access guide wire are not needed. This embodiment reduces the number of steps required to access the artery, and in some circumstances may be desirable to the user.

Alternately, the sheath dilator is a two-part sheath dilator assembly 260 as shown in FIG. 15, with an inner dilator 269 and an outer dilator 270. The outer dilator 270 is configured to receive an 0.035" sheath guide wire 300 and to provide a smooth transition from the 0.035" wire to the access sheath 220. The inner dilator 269 is configured to receive a smaller guide wire in the range 0.014" to 0.018" and to provide a smooth transition from the smaller guide wire to the outer dilator 270. Once the sheath guidewire is positioned in the CCA, the access sheath and outer sheath dilator 270 are inserted over an 0.035" sheath guidewire 300 into the CCA. The guidewire is then removed and an inner sheath dilator 269 is inserted into the outer sheath dilator. In an embodiment, the inner sheath dilator has an angled tip 276 as seen in FIG. 16. An interventional 0.014" guide wire is inserted through the inner sheath dilator and is directed to the target treatment site using the angled tip to aid in guide wire positioning. Alternately, the inner sheath dilator has a straight tip and is used to aid in positioning the guide wire safely into the CCA. Once the 0.014" wire is positioned at or across the target treatment site, the sheath dilator 260 and sheath 0.035" guide wire 300 are then removed, and the intervention proceeds.

In an alternate embodiment, the sheath dilator is a two lumen sheath dilator 1705. In this embodiment, the sheath and dilator are inserted over the sheath guide wire 300, with the sheath guidewire positioned in the larger lumen 1805 of dilator 1705. Once the sheath and dilator is in place, an interventional 0.014" guide wire is positioned through the smaller lumen 1815. The dilator provides distal support and maintains the position of the sheath tip in the axial direction of the vessel lumen, thus allowing a potentially safer and easier advancement of the 0.014" wire than if the dilator were removed and the sheath tip was directed at least partially towards to posterior wall of the artery. Once the 0.014" wire is positioned at or across the target treatment site, the sheath dilator 1705 and sheath guide wire 0.035" are then removed, and the intervention proceeds.

In yet another embodiment, it may be desirable to occlude the CCA during the intervention to minimize antegrade flow of emboli. In this embodiment, the occlusion step may be performed via vascular surgical means such as with a vessel loop, tourniquet, or vascular clamp. In an alternate embodiment, the access sheath 220 has an occlusion element such as an occlusion balloon 250 on the distal tip. In this embodiment, the balloon is inflated when CCA occlusion is desired. In a further variant, while the CCA is occluded either surgically or via balloon occlusion, it may be desirable to connect the arterial sheath to a flow shunt, for example to create a reverse flow system around the area of the treatment site to minimize distal emboli. In this embodiment, the arterial sheath 220 has a Y connection to a flow line 256. The flow line may be connected to a return site with a pressure lower than arterial pressure to create a pressure gradient that results in reverse flow through the shunt, for example an external reservoir or a central venous return site like the femoral vein or the internal jugular vein. Alternately, the flow line may be connected to an aspiration source such as an aspiration pump or syringe.

In another embodiment, a transcarotid access system is used to perform a percutaneous neurointerventional procedure. In this embodiment, the user performs a percutaneous puncture of the common carotid artery CCA with an access needle 120 at the desired access site. Ultrasound may be used to accurately identify a suitable access site and guide the needle puncture. An access guide wire 140 is inserted through the needle into the common carotid artery and advanced into the CCA. The access needle 120 is removed and a micro access cannula 160 is inserted over the wire 140 into the CCA. The user removes the cannula inner dilator 168 and guide wire 140, leaving the cannula 162 in place. If desired, the user performs an angiogram through the cannula 162. The user then places sheath guide wire 300 through the cannula, using guide wire markings 318 to aid in desired insertion length. The cannula 162 is removed from the guidewire and the access sheath 220 and sheath dilator 260 are inserted as an assembly over the sheath guidewire 300 into the CCA.

Alternately, the smaller access guide wire 140 is used to position the access sheath 220 and sheath dilator 260 into the CCA. In this embodiment, the sheath dilator tapered tip 266 has been configured to transition smoothly from the access guide wire 140 to the access sheath 220. In one variant, the access needle is 21G and the access guide wire is 0.018". In another variant, the access needle is 24G and the access guide wire is 0.014". Once the sheath is placed, the guide wire and sheath dilator are removed and an interventional procedure is then performed by introduction of interventional devices through hemostasis valve 226 on the proximal end of the arterial sheath and to the desire treatment site. Contrast injections may be made as desired during the procedure via the flush arm 228 on the arterial sheath 220.

Alternately, it may be desirable once the sheath is placed in the CCA to advance it further into the ICA, for example in the mid to distal cervical ICA, petrous ICA or further distally. In this embodiment, the sheath dilator may be replaced with a softer sheath dilator so that the sheath may be advanced without risk of damaging the distal ICA. In this embodiment, the softer dilator has a distal radiopaque marker so that the user may easily visualize the leading edge of the sheath and dilator assembly during positioning of the sheath. Once the access sheath is positioned, the dilator and sheath guide wire may be removed and the intervention can proceed. Alternately, once the sheath is placed in the CCA, the 0.035" guide wire may be removed and an inner dilator with a smaller guide wire in the range 0.014" to 0.018" may be inserted into sheath dilator. The sheath dilator assembly with the inner dilator and smaller guide wire may be then positioned more distally in the ICA with reduced risk of vessel trauma.

In an embodiment, it may be desirable to occlude the CCA or ICA during portions of the procedure to reduce the chance of distal emboli flowing to the brain. In this embodiment, the CCA or ICA is occluded by means of an occlusion balloon 250 on the access sheath 220. It may also be desireable to connect the arterial sheath to a flow shunt, for example to create a reverse flow system around the area of the treatment site to minimize distal emboli. In this embodiment, the arterial sheath 220 has a Y connection to a flow line 256. The flow line may be connected to a return site with a pressure lower than arterial pressure to create a pressure gradient that results in reverse flow through the shunt. Alternately, the flow line may be connected to an aspiration source such as an aspiration pump or syringe.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. A method for introducing an interventional device into a common carotid artery, the method comprising:
   collectively introducing an arterial access sheath and a first dilator into a common carotid artery via a carotid access needle puncture site, wherein the first dilator is positioned within the arterial access sheath, wherein:
   a) the arterial access sheath includes a sheath body sized and shaped to be introduced into the common carotid artery via the carotid artery access site, the sheath body defining an internal lumen that provides a passageway for introducing a catheter into the common carotid artery when the sheath body is positioned in the common carotid artery; and
   b) the first dilator has a tapered distal tip sized and shaped to dilate the needle puncture site to a larger diameter for insertion of the arterial access sheath into the artery, the first dilator having an internal lumen to allow the dilator to be inserted over a sheath guidewire into an artery, wherein at least a portion of the first dilator has a first bending stiffness;
   removing the first dilator from the arterial access sheath; and
   introducing an elongated second dilator into the internal lumen of the sheath body while the sheath body is positioned within the common carotid artery, the second dilator having a tapered distal tip, the second dilator having an internal lumen to allow the second dilator to be inserted over a guidewire into an artery, wherein the second dilator has a distal region having a second bending stiffness less than the first bending stiffness of the first dilator.

2. A method as in claim 1, wherein the first dilator has a distal section that is more flexible than a proximal section of the first dilator so as to accommodate a steep insertion angle into an artery.

3. A method as in claim 2, wherein the distal section of the first dilator is 2 to 5 cm in length.

4. A method as in claim 2, wherein the distal section of the first dilator is 20% to 50% more flexible than the proximal section of the first dilator.

5. A method as in claim 1, wherein the distal region of the second dilator is more flexible than a distal section of the first dilator.

6. A method as in claim 1, wherein the distal region of the second dilator is 2 to 5 cm in length.

7. A method as in claim 1, wherein the distal region of the second dilator is 20% to 50% more flexible than a proximal region of the second dilator.

8. A method as in claim 1, wherein the second dilator has an intermediate mid portion that provides a smooth transition in stiffness between a proximal region of the second dilator and the distal region of the second dilator.

9. A method as in claim 1, wherein a distal region of the first dilator has a bending stiffness in the range of 50 to 100 $N\text{-}mm^2$ and the distal region of the second dilator has a bending stiffness in the range of 5 to 15 $N\text{-}mm^2$.

10. A method as in claim 1, further comprising a radiopaque tip marker on at least one of the first and second dilators.

11. A method as in claim 1, wherein the internal lumen of the second dilator has a diameter that is smaller than a diameter of the internal lumen of the first dilator.

12. A method as in claim 1, wherein the internal lumen of the first dilator accommodates a guidewire of 0.035 to 0.038 inch in diameter and the internal lumen of the second dilator accommodates a guidewire of 0.014 to 0.018 inch in diameter.

13. A method as in claim 1, wherein a proximal region of at least one of the first dilator and the second dilator includes a hub having a side opening that provides access to the internal lumen of the respective dilator to permit insertion and removal of a guidewire into or from the internal lumen of the respective dilator.

14. A method as in claim 13, wherein the hub includes a sleeve that moves between a first position that covers the side opening and a second position that does not cover the side opening.

15. A method as in claim 1, wherein the second dilator is a two-part dilator formed of an outer dilator and one or more inner dilators that slidably attach to the outer dilator in a co-axial arrangement.

16. A method as in claim 15, wherein the outer dilator accommodates a guidewire of 0.035 to 0.038 inch in diameter and inner dilator accommodates a guidewire of 0.014 to 0.018 inch in diameter.

17. A method as in claim 15, wherein the inner and outer dilators include proximal hubs that lock to one another to lock the inner and outer dilators to one another.

18. A method as in claim 15, wherein at least one of the inner dilators has an angled tip that angles away from a longitudinal axis of the respective dilator.

19. A method as in claim 1, wherein the sheath body has a proximal section and a distalmost section that is more flexible than the proximal section, and wherein a ratio of an entire length of the distalmost section to an overall length of the sheath body is one tenth to one half the overall length of the sheath body.

20. A method as in claim 1, wherein the sheath body has a proximal section and a distalmost section that is more flexible than the proximal section, and wherein the distalmost section is 2.5 to 5 cm in length and the overall sheath body is 20 to 30 cm in length.

21. A method as in claim 1, wherein the sheath body has a proximal section and a distalmost section that is more flexible than the proximal section and a transition section between the distalmost flexible section and the proximal section, and wherein the distalmost section is 2.5 to 5 cm in length, the transition section is 2 to 10 cm in length, and the overall sheath body is 20 to 30 cm in length.

22. A method as in claim 1, wherein at least one of the first and second dilators is configured to lock to the arterial access sheath when positioned in the internal lumen of the arterial access sheath.

* * * * *